(12) United States Patent
Platscher et al.

(10) Patent No.: US 11,510,988 B2
(45) Date of Patent: Nov. 29, 2022

(54) TARGETING AMINOACID LIPIDS

(71) Applicant: Merck Patent GmbH, Darmstadt (DE)

(72) Inventors: Michael Platscher, Schlatt (CH); Raymond Behrendt, Singen (DE); Viola Groehn, Dachsen (CH); Simone Hoertner, Zurich (CH); Marco Passafaro, Thayngen (CH); Finn Bauer, Bedford, MA (US)

(73) Assignee: Merck Patent GmbH, Darmstadt (DE)

( * ) Notice: Subject to any disclaimer, the term of this patent is extended or adjusted under 35 U.S.C. 154(b) by 701 days.

(21) Appl. No.: 15/867,985

(22) Filed: Jan. 11, 2018

(65) Prior Publication Data

US 2018/0133334 A1    May 17, 2018

Related U.S. Application Data

(63) Continuation of application No. 14/384,702, filed as application No. PCT/EP2013/000698 on Mar. 11, 2013, now Pat. No. 9,878,044.

(30) Foreign Application Priority Data

Mar. 16, 2012    (EP) .................................. 12001803

(51) Int. Cl.
*A61K 47/60*    (2017.01)
*A61K 47/54*    (2017.01)
(Continued)

(52) U.S. Cl.
CPC ............ *A61K 47/60* (2017.08); *A61K 47/543* (2017.08); *A61K 47/6911* (2017.08);
(Continued)

(58) Field of Classification Search
CPC ........................................................ A61K 47/60
See application file for complete search history.

(56) References Cited

U.S. PATENT DOCUMENTS

| 4,634,504 A | 1/1987 | Bechem et al. |
| 5,108,921 A | 4/1992 | Low et al. |

(Continued)

FOREIGN PATENT DOCUMENTS

| EP | 0142010 A1 | 5/1985 |
| WO | 79/00515 A1 | 8/1979 |

(Continued)

OTHER PUBLICATIONS

International Search Report from PCT/EP2013/000698 dated Jul. 23, 2013.
(Continued)

*Primary Examiner* — Benjamin J Packard
(74) *Attorney, Agent, or Firm* — Millen White Zelano and Branigan, PC; Csaba Henter

(57) ABSTRACT

The present invention is directed to carrier systems comprising ether-lipids conjugated to one or more bioactive ligands and exposed on the surface of the carrier system for use in targeted delivery and/or antigen display systems. Optionally one or more further bioactive agents may be encapsulated or embedded within or attached to or adsorbed onto the carrier system. The present invention is further directed to methods of their preparation and their uses in medical applications, such as targeted delivery of bioactive agents to specific tissues or cells and antigen display systems for the study, diagnosis, and treatment of traits, diseases and conditions that respond to said bioactive agents.

36 Claims, 2 Drawing Sheets

$*p < 0.01$

(51) Int. Cl.
*A61K 47/69* (2017.01)
*C07D 475/04* (2006.01)
*C07C 237/06* (2006.01)
*C07C 237/30* (2006.01)
*C07K 5/02* (2006.01)
*C07K 7/08* (2006.01)
*C07K 7/64* (2006.01)

(52) U.S. Cl.
CPC .......... *C07C 237/06* (2013.01); *C07C 237/30* (2013.01); *C07D 475/04* (2013.01); *C07K 5/02* (2013.01); *C07K 7/08* (2013.01); *C07K 7/64* (2013.01)

(56) References Cited

U.S. PATENT DOCUMENTS

| | | | |
|---|---|---|---|
| 5,416,016 | A | 5/1995 | Low et al. |
| 5,498,632 | A | 3/1996 | Santaniello et al. |
| 5,498,633 | A | 3/1996 | Santaniello et al. |
| 5,512,439 | A | 4/1996 | Hornes et al. |
| 5,635,382 | A | 6/1997 | Low et al. |
| 5,820,847 | A | 10/1998 | Low et al. |
| 6,030,954 | A | 2/2000 | Wu et al. |
| 6,056,973 | A | 5/2000 | Allen et al. |
| 6,214,388 | B1 | 4/2001 | Benz et al. |
| 6,306,993 | B1 | 10/2001 | Rothbard et al. |
| 6,335,434 | B1 | 1/2002 | Guzaev et al. |
| 6,495,663 | B1 | 12/2002 | Rothbard et al. |
| 6,861,514 | B2 | 3/2005 | Cook et al. |
| 6,936,272 | B2 | 8/2005 | Martin et al. |
| 7,122,202 | B2 | 10/2006 | Allen et al. |
| 7,135,177 | B2 | 11/2006 | Benz et al. |
| 7,507,407 | B2 | 3/2009 | Benz et al. |
| 7,608,591 | B2 * | 10/2009 | Liu .................. A61K 47/67 514/1.1 |
| 7,871,620 | B2 | 1/2011 | Benz et al. |
| 2001/0016196 | A1 | 8/2001 | Benz et al. |
| 2001/0038851 | A1 | 11/2001 | Allen et al. |
| 2002/0049163 | A1 | 4/2002 | Cook et al. |
| 2002/0131965 | A1 | 9/2002 | Rothbard et al. |
| 2002/0172711 | A1 | 11/2002 | Martin et al. |
| 2003/0138490 | A1 | 7/2003 | Hu et al. |
| 2003/0162719 | A1 | 8/2003 | Rothbard et al. |
| 2003/0215490 | A1 | 11/2003 | Allen et al. |
| 2004/0191250 | A1 | 9/2004 | Allen et al. |
| 2004/0191307 | A1 | 9/2004 | Allen et al. |
| 2005/0063979 | A1 | 3/2005 | Pickl et al. |
| 2005/0136064 | A1 | 6/2005 | Allen et al. |
| 2005/0169980 | A1 | 8/2005 | Allen et al. |
| 2006/0111274 | A1 | 5/2006 | Rothbard et al. |
| 2006/0246126 | A1 | 11/2006 | Allen et al. |
| 2007/0031484 | A1 | 2/2007 | Benz et al. |
| 2007/0292354 | A1 | 12/2007 | Port |
| 2010/0028450 | A1 | 2/2010 | Vasu |
| 2010/0068255 | A1 | 3/2010 | Benz et al. |
| 2010/0104629 | A1 | 4/2010 | Dande |

FOREIGN PATENT DOCUMENTS

| | | | |
|---|---|---|---|
| WO | 98/52614 | A2 | 11/1998 |
| WO | 99/66063 | A2 | 12/1999 |
| WO | 01/22995 | A1 | 4/2001 |
| WO | 02/072068 | A2 | 9/2002 |
| WO | 02/094185 | A2 | 11/2002 |
| WO | 03/039594 | A2 | 5/2003 |
| WO | 2006/032705 | A2 | 3/2006 |
| WO | 2007/087341 | A2 | 8/2007 |
| WO | 2009129387 | A1 | 10/2009 |

OTHER PUBLICATIONS

Theresa M. Allen et al. "A new strategy for attachment of antibodies to sterically stabilized liposomes resulting in efficient targeting to cancer cells" Biochimica et Phiophysica Acta, 1237, [1995], pp. 99-108.
G. Blume et al. "Specific targeting with poly(ethylene glycol)-modified liposomes: coupling of homing devices to the ends of the polymeric chains combines effective target binding with long circulation times" Biochimica et Biophysica Acta, 1149, [1993], pp. 180-184.
Samuel Zalipsky "Functionalized Poly(ethylene glycol) for Preparation of Biologically Relevant Conjugates", Bioconjugate Chem., 6, [1995], pp. 150-165.
Igor Solodin et al. "A Novel Series of Amphiphilic Imidazolinium Compounds for in Vitro and in Vivo Gene Delivery", Biochemistry, 34, [1995], pp. 13537-13544.
Jiin H. Felgner, et al. "Enhanced Gene Delivery and Mechanism Studies with a Novel Series of Cationic Lipid Formulations" The Journal of Biological Chemistry, vol. 269, No. 4, [1994], pp. 2550-2561.
Louise M. Canfield et al. "Incorporation of β-Carotene into Mixed Micelles", Methods in Enzymology, vol. 189, [1990], pp. 418-422.
Mohamed El-Gorab et al. "Solubilization of β-Carotene and retinol into aqueous solutions of mixed micelles", Biochimica et Biophysica Acta, 306, [1973], pp. 58-66.
Kozo Shinoda "The Formation of Micelles" Academia Press, N.Y. [1963], Chapter 1, pp. 1-88.
Janos H. Fendler et al. "Catalysis in Micellar and Macromolecular Systems" Department of Chemistry, Texas A&M University College Station, Texas, Academic Press, [1975] (cover and contents list of book-5 pages).
George Kokotos et al. "Synthesis of 2-Oxo Amide Triacylglycerol Analogues and Study of Their Inhibition Effect on Pancreatic and Gastric Lipases" Chem. Eur J., vol. 6, No. 22, [2000], pp. 4211-4217.
David I. Magee, et al. "Use of the Ramberg-Backlund Rearrangement for the Synthesis of Medium and Large Heterocyclic Alkenes: Stereoselective Olefin Formation" J. Org. Chem., 65, [2000], pp. 8367-8371.
Shan S. Wong et al. "Chemistry of Protein and Nucleic Acid Cross-Linking and Conjugation" CRC Press, Second Edition, [1991], (cover and contents list of book-10 pages).
Greg T. Hermanson "Bioconjugate Techniques" Academic Press, [1996], (cover and contents list of book-18 pages).
Gordon F. Bickerstaff "Immobilization of Enzymes and Cells" Humana Press [1997], (cover and contents list of book-5 pages).
E. Atherton et al. "Application of Polyamide Resins to Polypeptide Synthesis: an Improved Synthesis of β-Endorphin Using Fluorenylmethoxycarbonylamino-acids" J.C.S. Chem. Comm., [1978], pp. 539-540.
James A. Heyes et al. "Synthesis of Novel Cationic Lipids: Effect of Structural Modification on the Efficiency of Gene Transfer" J. Med. Chem., vol. 45, No. 1, [2002], pp. 99-114.
M. Wang et al. "Targeting nanoparticles to cancer" Pharmacological Research 62, [2010], pp. 90-99.
Office Action in corresponding Brazilian application BR112014022451-0 dated Jan. 5, 2022 (pp. 1-6).

* cited by examiner

* p < 0.01

TARGETING AMINOACID LIPIDS

FIELD OF THE INVENTION

The present invention is directed to carrier systems comprising ether-lipids conjugated to one or more bioactive ligands (and exposed on the surface of the carrier system) for use in targeted delivery and/or antigen display systems, which carrier systems may comprise one or more further bioactive agents. The present invention is further directed to methods of their preparation and their uses in medical applications, such as targeted delivery of said bioactive agents to specific tissues or cells and antigen display systems for the study, diagnosis, and treatment of traits, diseases and conditions that respond to said bioactive agents.

BACKGROUND OF THE INVENTION

Molecular recognition, such as between receptor ligand, antigen-antibody, DNA-protein, sugar-lectin, RNA-ribosome, etc. is an important principle underlying many biological systems and is being applied to many artificially created biological systems for use in medical applications, such as in artificial (micro- or nano-) particulate systems including polymeric beads, vesicular lipids, microemulsions, and the like.

One important example of a molecular recognition based application is the use of targeted delivery of diagnostic or therapeutic compounds, such as antiviral, chemotherapeutic or imaging agents, to specific sites, which allows to overcome the limitations associated with nonspecific delivery (such as in vivo clearance time, potential toxicity, problems associated with membrane transport of an agent and the like) and thus greatly increases their effectiveness. Various recognition-based strategies have been used to improve the delivery of compounds into the intracellular environment (i.e. to specific cell compartments) of a target cell to exert its biological activity, in particular delivery through specific transporters involving the use of biological or artificial carriers, such as viral vectors, cationic polymers, such as polylysine, polyarginine and the like (see, e.g. WO 79/00515, WO 98/52614), lipid carriers, and various other conjugate systems.

One widely used approach involves the use of lipid vesicles as artificial carriers, e.g. liposomes and micelles, which have been extensively developed and analyzed as drug delivery vehicles due to their ability to reduce systemic exposure of a bioactive agent, thereby overcoming problems associated with degradation, solubility, etc. and providing an increase in blood circulation times. Actively targeted delivery of a bioactive agent involves derivatizing the lipids of the lipid vesicle (either prior or after vesicle formation) with a targeting ligand that serves to direct (or target) the vesicle to specific cell types such as cancer cells or cells specific to particular tissues and organs, such as hepatocytes, after in vivo administration (see, for example, U.S. Pat. Nos. 6,316,024 and 6,214,388; Allen et al., Biochim. Biophys. Acta, 1237:99-108 (1995); Blume et al., Biochim. Biophys. Acta, 1149:180-184 (1993)). This may be accomplished by utilizing receptors that are overexpressed in specific cell types, which include for example folic acid receptor (FR) (overexpressed in a variety of neoplastic tissues, including breast, ovarian, cervical, colorectal, renal, and nasoparyngeal tumors), transferrin receptor (TfR) (overexpressed on metastatic and drug resistant cells of most carcinomas, sarcomas and some lymphomas and leukaemias), epidermal growth factor receptor (EGFR) (overexpressed in anaplastic thyroid cancer and breast, lung and colorectal tumors), vascular endothelial growth factor receptor 1 and 2 (VEGFR-1/2) (highly expressed on endothelial cells in tumor neovasculature), metastin receptor (overexpressed in papillary thyroid cancer), ErbB family receptor tyrosine kinases (overexpressed in a significant subset of breast cancers), human epidermal growth factor receptor-2 (Her2/neu) (overexpressed in breast cancers), tyrosine kinase-18-receptor (c-Kit) (overexpressed in sarcomatoid renal carcinomas), HGF receptor c-Met (overexpressed in esophageal adenocarcinoma), CXCR4 and CCR7 (overexpressed in breast cancer), endothelin-A receptor (overexpressed in prostate cancer), peroxisome proliferator activated receptor delta (PPAR-delta) (overexpressed in most colorectal cancer tumors), PDGFR A (overexpressed in ovarian carcinomas), BAG-1 (overexpressed in various lung cancers), soluble type II TGF beta receptor (overexpressed in pancreatic cancer), asialoglycoprotein receptor (overexpressed on hepatocytes), $\alpha_v\beta_3$ integrin receptor (overexpressed in growing tumor vascularture), legumain (a clan CD cysteine protease enriched in solid tumor tissue and overexpressed on TAMs, tumor associated macrophages), etc.

Any agent which selectively binds to such a specific receptor cell or tissue to be treated or assayed may be attached to a lipid vesicle and act as a targeting or receptor ligand. Typically, such targeting ligands have been attached to a lipid or lipid vesicle surface through a long chain (e.g. polymeric) linker. For example folic acid based conjugates have been used to provide a targeted delivery approach of a therapeutic compound useful for the treatment and/or diagnosis of a disease, allowing a reduction in the required dose of therapeutic compounds (see e.g. WO 02/094185, U.S. Pat. No. 6,335,434, WO 99/66063, U.S. Pat. No. 5,416,016). Likewise, the use of galactose- and galactosamine-based conjugates to transport exogenous compounds across cell membranes can provide a targeted delivery approach to the treatment of liver disease such as HBV and HCV infection or hepatocellular carcinoma while allowing a reduction in the required dose of therapeutic compounds required for treatment (see e.g. U.S. Pat. No. 6,030,954, . . . ).

Another important example of a molecular recognition based aplication is the use of antigen display systems which involve presentation of both "self" and "foreign" proteins (antigens) to the immune system to generate T cell activation, modulation or tolerance. The receptor ligand interactions in antigen-presenting systems that contribute to the desired immune response or absence thereof are complex and difficult to assess, being influenced by various parameters such as ligand densities, presence of coreceptors, receptor ligand affinities and surface conditions. Thus a widely used approach involved using naturally occurring human cells (or parts thereof) whose primary function is antigen processing and presentation. But, while live cell based systems may be optimal for mimicking cell-cell interaction to achieve the desired induction of tolerance or immune response, they are dependent on a regulated expression of the surface molecules including possibly expression of additional "costimulatory" and/or adhesion molecules on its surface membrane at a sufficient therapeutic level. Currently known artificial systems range from genetically engineered subcellular antigen presenting vesicles, which carry the molecules required for antigen presentation and T-lymphocyte activation or inhibition on their surface (WO 03/039594) to systems on the basis of cell-sized, biodegradable microspheres based, antigen presenting system (WO 07/087341).

Clearly, there are still drawbacks to the above, molecular recognition based technologies and there remains a need in the art for a versatile and efficient artificial carrier system for use in molecular recognition based applications such as targeted delivery or antigen presentation, including simple and economic methods of their preparation.

The present application provides conjugates comprising ether-lipids having one or more covalently attached bioactive ligands as well as various carrier systems comprising these conjugates (and optionally further comprising one or more bioactive agents), which allow to overcome the limitations described above.

SUMMARY OF THE INVENTION

The present invention is directed to carrier systems comprising ether-lipids conjugated with one or more bioactive ligands for use in targeted delivery and/or antigen display systems. The one or more bioactive ligands are covalently attached to the ether-lipids of general formula I and exposed on the surface of a carrier system. Optionally at least one bioactive agent may be encapsulated or embedded within or attached to or adsorbed onto the surface of the carrier system.

Thus, in one aspect the invention is directed to a lipidic carrier system in form of a vesicle, such as a liposome or a micelle, comprising at least one lipid-ligand conjugate of formula I, optionally in admixture with further co-lipids. The at least one lipid-ligand conjugate comprises at least one ether-lipid which is covalently linked to at least one bioactive ligand, such as an antigen ligand, a target ligand, a therapeutic ligand or a diagnostic ligand. Optionally, at least one further bioactive agent is encapsulated or embedded in the internal void or bilayer (membrane) or attached to or adsorbed onto the surface of the vesicle. In some embodiments the vesicle is a liposome or a micelle.

In another aspect the invention is directed to a nanoparticulate carrier system in form of a lipid-coated particle having an internal void or a solid core, wherein the particle is coated with at least one lipid-ligand conjugate of formula I, optionally in admixture with further co-lipids. The at least one lipid-ligand conjugate of formula I comprises at least one ether-lipid which is covalently linked to at least one bioactive ligand, such as an antigen ligand, a target ligand, a therapeutic ligand or a diagnostic ligand. In some embodiments the nanoparticulate material is a lipid-coated nanoparticle or a nanosphere. Optionally at least one further bioactive agent is encapsulated in the internal void or embedded or dispersed in the solid core.

In another aspect the invention is also directed to the lipid-ligand conjugates themselves according to formula I, comprising an ether-lipid characterized by at least two ether-linked hydrocarbon chains and a headgroup having a short, straight-chain amino acid with up to 6 carbon atoms and up to three coupling sites to which at least one bioactive ligand may be covalently attached.

The lipid-ligand conjugates relate to a compound of general formula I

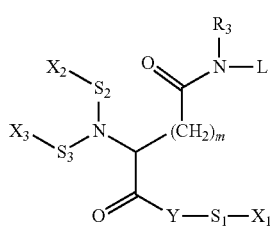

wherein
Y represents O, N, S or a covalent bond,
$S_1$, $S_2$, $S_3$ represent independently of each other a covalent bond or a spacer group,
$X_1$, $X_2$, $X_3$ represent independently of each other H or a ligand group
L is a group of formula (a)

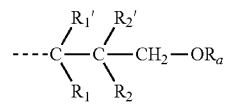

wherein the dashed line represents the linkage to N,
$R_1$ represents H or a group of formula $—(CH_2)_2—OR_{b1}$,
represents H or a group of formula $—(CH_2)_2—OR_{b2}$,
$R_2$ represents H or a group of formula $—CH_2—OR_c$,
$R_{2'}$ represents H or a group of formula $—OR_d$ or $—CH_2—OR_d$,
$R_3$ represents H or a group of formula $—(CH_2)_2—OR_e$ or $—(CH_2)_3—OR_e$,
$R_a$, $R_{b1}$, $R_{b2}$, $R_c$, $R_d$, $R_e$ represent independently of each other a saturated or unsaturated, straight or branched hydrocarbon chain,
m is 1, 2 or 3,
with the proviso that at least one of $R_1$, $R_{1'}$, $R_2$, $R_{2'}$, $R_3$ is not H and at least one of $X_1$, $X_2$, $X_3$ is a ligand group.

In specific embodiments the ligand group is a targeting ligand or an antigenic ligand or a therapeutic ligand or a diagnostic ligand.

Preferably, the targeting ligand is a pteroic acid derivative, a peptide and derivatives thereof, a polypeptide, a protein or a carbohydrate and the antigenic ligand is a peptide, protein or a carbohydrate.

In a further aspect, the invention is also directed to uses of carrier systems of the invention as a drug delivery system, diagnostic system or antigen display system. Also provided are kits for preparing the carrier systems containing the lipids of the invention and pharmaceutical formulations containing these carrier systems.

In other aspects the present invention is also directed towards methods for the treatment or for diagnosis of a disease comprising administering an effective amount of a carrier system of the invention.

In yet further aspects the present invention is also directed towards methods for modulating an immune response comprising administering an effective amount of a carrier system of the invention.

Other aspects of the invention include methods for transport of a biologically active compound across a membrane and/or methods of delivery of a biologically active compound into a cell using carrier systems of the invention

BRIEF DESCRIPTION OF THE DRAWINGS

The extent of cellular uptake for RGD decorated liposomes (obtained in Example 9) on M21 cells are evaluated on the basis of NBD-DOPE signal detected by Guava easyCyte 8HT flowcytometer and is illustrated in FIG. 1 and Table 1.

DETAILED DESCRIPTION OF THE INVENTION

Figure 1:
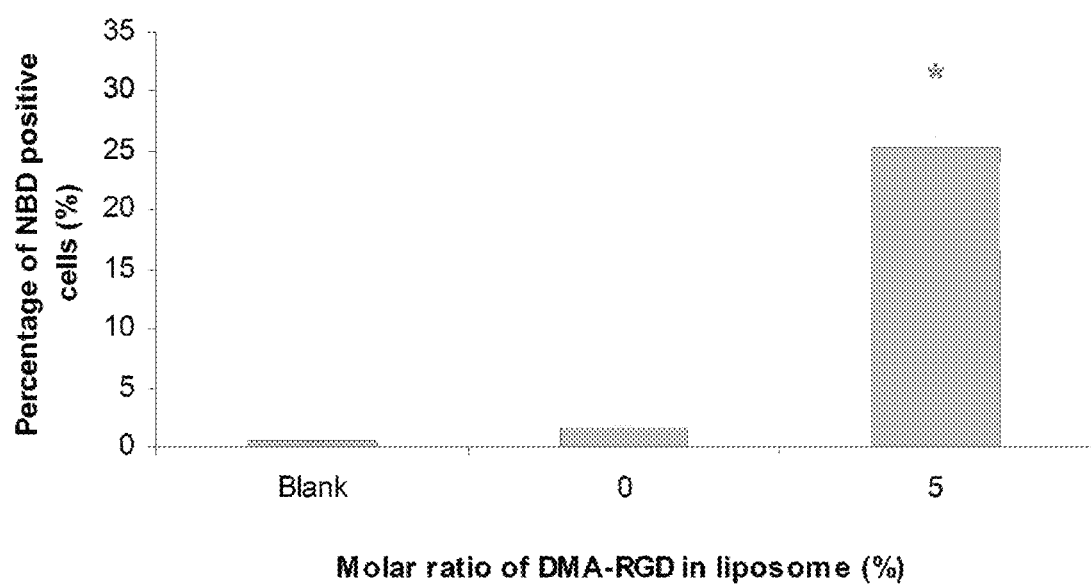
FIG. 1. Cellular uptake of an RGD targeting liposome (comprising 5% DMA-RGD) as compared to non-targeting liposome (comprising no DMA-RGD).

The present invention provides carrier systems comprising at least one ether-lipid and at least one bioactive ligand conjugated to said ether-lipid to form a lipid-ligand conjugate of the invention. Any carrier system which can be formed of or coated with lipid-ligand conjugates of general formula I optionally in combination with other lipidic matrix compounds (or co-lipids) may act as a carrier system according to the present invention. Typically, a carrier system of the invention is based on a microparticulate or nanoparticulate material in various shapes and forms, such as vesicles or spheres with an internal void, particles with a solid core, rods, tubes, clusters and the like. In some embodiments, a carrier system according to the invention is a lipidic carrier system, such as a liposome, a micelle, wherein the lipid-ligand conjugate is forming, optionally together with other matrix lipids, the lipid wall of the vesicle. In other embodiments, a carrier system according to the invention is a nanoparticulate carrier system, such as a nanoparticle, a nanosphere, a nanocluster, a nanotube, a polymeric bead, and the like, wherein the lipid-ligand conjugate is adsorbed, optionally together with other matrix lipids, as a coating on the surface of the nanoparticulate carrier system. Depending on the nature and intended use of a carrier system according to the invention, one or more bioactive agents may be encapsulated or embedded within or attached to or adsorbed onto the surface of the carrier system.

As used herein, the term "bioactive" refers to an ability to elicit a biological response that is sought in a cell, tissue, system, and/or subject (including a human being). The term "biological response" refers to the physiological reaction of a cell to a stimulus, and thus could be any cellular, neurological, chemical, inflammatory, immunologic or pathologic biological response, process or reaction by the subject. The response, process or reaction can be chemical, cellular, neurological, psychological or the like. Thus, the term "bioactive ligand or bioactive ligand group" or simply "ligand" or "ligand group" as used herein refers to a ligand which elicits such a biological response and which is used for covalent attachment to an ether-lipid of general formula I either directly or via a spacer group (using standard chemical coupling techniques). A bioactive ligand may be a targeting ligand, an antigenic ligand, a therapeutic ligand or a diagnostic ligand.

The term "bioactive agent" or simply "agent" as used herein refers to any synthetic or naturally occurring compound (in free form, salt form or solvated or hydrated form) having a biological activity, such as a targeting agent, an antigenic agent, a therapeutic agent or a diagnostic agent, preferably a therapeutic agent or a diagnostic agent.

It is understood that the definitions of the various bioactive agent groups and bioactive ligand groups may be overlapping.

Thus, the expression "targeting" used in conjunction with "agent" or "ligand" (for uses in targeted delivery systems) refers to a compound which is capable of interacting with a complementary binding moiety at a desired location and/or under desired conditions. For example, complementary binding moieties can be ligands and anti-ligands (e.g. streptavidin and biotin, protein A or G and Fc region of immunoglobulins), ligands and receptors (e.g. small molecule ligands and their receptors, or sugar-lectin interactions), phage display-derived peptides, complementary nucleic acids (e.g. DNA hybrids, RNA hybrids, DNA/RNA hybrids, etc.), and aptamers. Other exemplary complementary binding moieties include, but are not limited to, moieties exhibiting complementary charges, hydrophobicity, hydrogen bonding, covalent bonding, Van der Waals forces, reactive chemistries, electrostatic interactions, magnetic interactions, etc.

A "targeting ligand" or "targeting agent" specific for a particular receptor (a receptor agent or ligand) refers to any compound which is a specific binding partner of a specific binding pair, wherein the other binding partner is a receptor. The receptor may be present attached to a cell membrane or surface or in soluble form and may be present intracellularly and/or extracellularly in a subject, preferably a mammalian subject, e.g. a human or animal. Examples of a receptor include, without limitation, membrane receptors, soluble receptors, cloned or recombinant receptors, clan CD cysteine protease and other proteases and other enzymes, hormone receptors, drug receptors, transmitter receptors, autocoid receptors, cytokine receptors, antibodies, antibody fragments, engineered antibodies, antibody mimics, molecular recognition units, adhesion molecules, agglutinins, integrins, and selectins. Typically, the binding affinity of a receptor ligand for its receptor may be at least $10^{-5}$M, preferably $10^{-7}$M and greater, e.g. around $10^{-5}$M to around $10^{-12}$M. Examples of a receptor agent or ligand include, without limitation, a peptide or polypeptide, including derivatives thereof such as aza-peptide derivatives or derivatives containing partially or only D-amino acids, a glycopeptide, and the like, a protein, including a glycoprotein or phosphoprotein, a carbohydrate, glycolipid, phospholipid, oligonucleotide, polynucleotide, aptamers, spiegelmers, vitamin (e.g. vitamin B9 or folic acid, vitamin B12), antigens and fragments thereof, haptens, receptor agonists, partial agonists, mixed agonists, antagonists, drugs, chemokines, hormones (e.g. LH, FSH, TRH, TSH, ACTH, CRH, PRH, MRH, MSH, glucagon and prolactin; transferrin; lactoferrin; angiotensin; histamine; insulin; lectins), transmitters, autocoids; growth factors (for example PDGF, VEGF, EGF, TGFa, TBFß, GM-CSF, G-CSF, M-CSF, FGF, IGF, bombesins, thrombopoietin, erythropoietin, oncostatin and endothelin 1), cytokines including interleukins (e.g. interleukins 1 to 15), lymphokines and cell signal molecules, such as tumor necrosis factor (e.g. tumour necrosis factors α and ß) and interferons (e.g. interferons α, ß and γ), prosthetic groups, coenzymes, cofactors, regulatory factors, or any other naturally occurring or synthetic organic molecule which can specifically bind to a receptor, including fragments, analogs and other derivatives thereof that retain the same binding properties. The choice of a receptor agent or ligand for use in the present invention will be determined by the nature of the disease, condition, or infection to be assayed and/or treated. Preferred receptor agents or ligands include vitamins (e.g. folic acid or fragments thereof), pteroic acid derivatives, peptides, including derivatives such as aza-peptide derivatives, proteins and carbohydrates. Most preferred are pteroyl derivativesand peptides in particular aza-peptide derivatives.

The term "pteroyl" or "pteroic acid" as used herein represents a condensed pyrimidine heterocycle, which is linked to an aminobenzoyl moiety. As used herein a "condensed pyrimidine heterocycle" includes a pyrimidine fused with a further 5- or 6-membered heterocycle, resulting in a pteridine or a pyrrolopyrimidine bicycle. Conjugation of a pteroyl group to one or more of the reactive sites on the headgroup of an ether lipid (N- or Y-group) will result in a folate structure, wherein the headgroup represents the glutamic acid part or a derivative thereof. Exemplary folate structures are based on a folate skeleton, i.e. pteroyl-glutamic acid resp. N-[4-[[(2-amino-1,4-dihydro-4-oxo-6-pteridinyl)methyl]amino]benzoyl]-L-glutamic acid, and derivatives thereof. Such folate derivatives include folates having optional substituents on reactive or non-reactive sites and/or wherein selected atoms have been replaced, e.g. selected heteroatoms, preferably one or two, have been replaced by carbon atoms (such as in deaza and dideaza analogs). Examples are optionally substituted folic acid, folinic acid, pteropolyglutamic acid, and folate receptor-binding pteridines such as tetrahydropterins, dihydrofolates, tetrahydrofolates, and their deaza and dideaza analogs. Folic acid, 5-methyl-(6S)-tetrahydrofolic acid and 5-formyl-(6S)-tetrahydrofolic acid are the preferred basic structures used for the compounds of this invention. The terms "deaza" and "dideaza" analogs refers to the art recognized analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5-dideaza, 5,10-dideaza, 8,10-dideaza, and 5,8-dideaza analogs. Preferred deaza analogs compounds include N-[4-[2-[(6R)-2-amino-1,4,5,6,7,8-hexahydro-4-oxopyrido[2,3-d]pyrimidin-6-yl]ethyl]benzoyl]-L-glutamic acid (Lometrexol) and N-[4-[1-[(2,4-diamino-6-pteridinyl)methyl]propyl]benzoyl]-L-glutamic acid (Edatrexate). In each of the above folate structure the glutamic acid portion is the portion corresponding to the headgroup of the ether-lipid and thus each of the above folate structures may also include the structures comprising the various glutamic acid derivatives corresponding to the headgroup.

The term "peptide" as used herein represents an oligopeptide consisting of 1 to 30, preferably of 2 to 20, most preferably of 3 to 10 amino acids. Peptides are typically connected through their N-terminus, C-terminus and/or through their side chains to the reactive positions at the head group (i.e. N- and/or Y-group) of an ether-lipid. Peptides may contain disulfide bridges as well as ester linkages. Furthermore, peptides may bear protecting groups at the N-terminus, C-terminus and in the side chains. The term "amino acid" includes natural occurring L-amino acids, D-amino acids, synthetic amino acids, beta amino acids and homologues thereof.

Preferred peptides as defined above for use in the present application include e.g. cell-specific ligands such as the RGD-peptide, NGR-peptide, ATWLPPR-peptide, APRPG-peptide, SMSIARL-peptide, TAASGVRSMH-peptide, LTLRWVGLMS-peptide, CDSDSDITWDQLWDLMK-peptide, GPLPLR-peptide, HWGF-peptide, and derivatives thereof (wherein the designation of the peptide is given in the single letter amino acid code), preferably the RGD peptide (i.e. the tripeptide amino acid sequence arginine-glycine-aspartic acid or Arg-Gly-Asp) and derivatives thereof. Derivatives of the RGD peptide include any structural modification to the peptide including a peptide containing the RGD sequence, as well as non-peptidic compounds comprising the RGD peptide.

The term "aza-peptide" as used herein refers to peptide analogs having a nitrogen atom substituted for one or more carbon atoms in the naturally occurring peptide structure. Aza-peptides typically consist of 1 to 30, preferably of 2 to 20, most preferably of 3 to 10 amino acids having a nitrogen atom substituted for at least one of the sp3-hybridized carbons, preferably for a carbon atom in alpha position of an amino acid, most preferably for the carbon atom in alpha position of the amino acid at the C-terminus. Aza-peptides are connected through their N-terminus, C-terminus and/or through their side chains to the reactive positions at the head group (i.e. N- and/or Y-group) of the ether-lipid. Aza-peptides may contain disulfide bridges as well as ester linkages. Furthermore, aza-peptides may bear protecting groups at the N-terminus, C-terminus and in the side chains. Preferred aza-peptides are derivatives of 2-azaasparagine, such as Cbz-alanylalanyl-2-azaasparagine (also known as RR11a) (Ekici et al., 2004, J. Med. Chem. 47, 1889-1892; WO 2012/031175 A9).

In other embodiments a targeting agent or ligand may also represent or comprise at least one blocking moiety. As used herein, the term "blocking moiety" refers to moieties which mask, block, cloak, and/or sterically inhibit the activity, self-recognition, and/or self-assembly of complementary binding moieties. For example, a blocking moiety is capable of blocking the ability of complementary binding moieties to interact with one another prior to a desired condition or time, when the blocking moiety is removed. A blocking moiety can include polymeric entities, such as polaxamines; poloxamers; polyethylene glycol (PEG); poly(lactic-co-glycolic acid)(PLGA), peptides; synthetic polymers and the like.

As used herein, the expression "antigen(ic)" used in conjunction with "agent" or "ligand" refers to a compound which provokes an immune response against itself or portions thereof. The term "immune response" refers to recognition of an antigen or parts thereof by an immune effector cell. This includes T cell mediated and/or B cell mediated immune responses that are influenced by modulation of T cell co-stimulation. The term immune response further includes immune responses that are indirectly effected by T cell activation such as antibody production (humoral responses) and the activation of other immune effector cells including, but not limited to, monocytes, macrophages, NK cells and cytotoxic T lymphocytes (CTLs), for example CTL lines, CTL clones, and CTLs from tumor, inflammatory, or other infiltrates. Certain diseased tissue express specific antigens and CTLs specific for these antigens have been identified. For example, approximately 80% of melanomas express the antigen known as gp-100. One of the most effective and desirable procedures to prevent microbial infections and pathogenic processes and thus combat such diseases are vaccines, which cause a stimulation of an immune response in a host organism prior to an actual infection or onset of a disease by introducing antigens or immunogens into the host organism.

A skilled person will understand that any macromolecule, including virtually any biological molecule (proteins, peptides, lipids, lipoproteins, glycans, glycoproteins, nucleic acids derivatives, such as oligonucleotides, polynucleotides, genomic or recombinant DNA) may serve as an antigen. An antigen may be synthesized chemically or biologically, or may be derived from recombinant or genomic DNA or can be derived from a biological sample, such as a tissue sample, a tumor sample, a cell or a biological fluid. Antigens may include, but are not limited to, viral antigens, bacterial antigens, fungal antigens, protozoal and other parasitic antigens, tumor antigens, antigens involved in autoimmune disease, addiction, allergy and graft rejection, and other miscellaneous antigens. Representative examples of an antigen may be a protein or peptide of bacterial, fungal, protozoan, or viral origin, or a fragment derived from these antigens, which include, but are not limited to, *Streptococcus* species, *Candida* species, *Brucella* species, *Salmonella* species, *Shigella* species, *Pseudomonas* species, *Bordetella* species, *Clostridium* species, Norwalkvirus, *Bacillus anthracis, Mycobacterium tuberculosis*, human immunodeficiency virus (UV), *Chlamydia* species, human Papillomaviruses, Influenza virus, Paramyxovirus species, Herpes virus, Cytomegalovirus, Varicella-Zoster virus, Epstein-Barr virus, Hepatitis viruses, *Plasmodium* species, *Trichomonas* species, sexually transmitted disease agents, viral encephalitis agents, protozoan disease agents, fungal disease agents, bacterial disease agents, cancer cells, or mixtures thereof.

Immunization of a subject may be enhanced by the use of multiple copies of an antigen as a multivalent display and is desirable in case of antigen ligands such as small peptides or carbohydrates, that are difficult to administer and generally fail to elicit an effective immune response due to the hapten-related size issues. Thus, as used herein, the term "multivalent" refers to the display of more than one copy or type of antigen on a carrier system.

The term "antigen-presenting system" or "antigen display system" as used herein refers to a naturally occurring or synthetic system, which (i) can present at least one antigen (or part thereof) in such a way that the at least one antigen (or part thereof) can be recognized or bound by an immune effector molecule, e.g. a T-cell antigen receptor on the surface of a T cell, or (ii) is capable of presenting at least one antigen (or part thereof) in the form of an antigen-MHC complex recognizable by specific effector cells of the immune system, and thereby inducing an effective cellular immune response against the antigen (or part thereof) being presented. In the context of the present invention, the term "recognized" refers to (i) a lipid compound conjugated to at least one antigenic ligand (or a composition or formulation thereof) which is recognized and bound by an immune effector cell wherein such binding is sufficient to initiate an effective immune response, or to (ii) a lipid compound conjugated to at least one targeting ligand (or a composition or formulation thereof) which is recognized and bound by its corresponding receptor or to a combination of both (a) and (b). Assays for determining whether a targeting or an antigenic ligand is recognized by a receptor or an immune effector cell, respectively, are known in the art and are described herein.

As used herein, the expression "therapeutic" used in conjunction with "agent" or "ligand" refers to a compound which is capable of exerting a biological effect in vitro and/or in vivo that is therapeutic in nature. A therapeutic ligand may be neutral or positively or negatively charged. Examples of suitable bioactive agents include pharmaceuticals and drugs, synthetic organic molecules, proteins, vitamins, steroids, siRNA, miRNA, adjuvants and genetic material.

The term "genetic material" refers generally to nucleosides, nucleotides, and polynucleotides, including deoxyribonucleic acid (DNA) and ribonucleic acid (RNA). The genetic material may be made by synthetic chemical methodology known to one of ordinary skill in the art, or by the use of recombinant technology, or by a combination of the two. The DNA and RNA may optionally comprise unnatural nucleotides and may be single or double stranded. "Genetic material" refers also to sense and anti-sense DNA and RNA, that is, a nucleotide sequence which is complementary to a specific sequence of nucleotides in DNA and/or RNA.

The term "pharmaceutical" or "drug" refers to any therapeutic or prophylactic agent which is used in the prevention, diagnosis, alleviation, treatment or cure of a disease or injury in a patient. It is understood that the bioactive agents to be entrapped or embedded in the lipid compositions or attached to or adsorbed onto the surface of the lipid compositions of the invention are not restricted to any particular class of biologically active material in terms of physicochemical properties, molecular size or the source of origin, i.e. synthetic, biotechnological materials, etc. Thus the pharmaceutical may be, for example, chosen from any of the following therapeutic class: analgesic, anesthetic, anti-Alzheimer's, anti-asthma agent, anti-Parkinsonism, antiallergic, antianginal, antiarrhythmic, antiarthritic, antiasthmatic, antibacterial, antibiotic, anticancer, anticoagulant, antidepressant, antidiabetic, antiemetic, antiepileptic, antifungal, antiglaucoma, anti-gout, antihistamine, antihyperprolactinemia, antihypertensive, antiinflammatory, antimigraine, antineoplastic, antiobesity, antiparasitic, anti-protozoal, antipyretics, antipsoriatic, antipsychotic, antithrombotic, antiulcer, antiviral, anxiolytic, benign prostatic hypertrophy, bronchodilator, calcium metabolism, cardiotonic, cardiovascular agent, chelator AND antidote, chemopreventive agent, contraception, diuretic, dopaminergic agent, gastrointestinal agent, gastroprokinetic, hematopoiesis, hemophilia, hormone, hormone replacement therapy, hypnotic, hypocholesterolemic, hypolipidemic, immunomodulator, immunostimulant, immunosuppressant, lipid regulating agent, male sexual dysfunction, multiple sclerosis, muscle relaxant, neuroleptic, nootropic, osteoporosis, phytoestrogen, platelet aggregation inhibitor, prostaglandin, radioenhencer for radiotherapy, relaxant and stimulant, respiratory distress syndrome, urinary incontinence, vasodilator, vitamin/nutritional, vulnerary and xanthine. Active agents belonging to these classes can be used in the previously mentioned compositions.

As used herein, the expression "diagnostic" used in conjunction with "agent" or "ligand" refers to a compound which is capable of diagnosing the presence or absence of a disease in a patient. The diagnostic agents may be neutral or positively or negatively charged. Examples of suitable diagnostic agents include, synthetic organic molecules and heavy metal complexes, such as contrast agents for use in connection with magnetic resonance imaging, ultrasound or computed tomography of a patient.

The choice of a targeting or antigenic or therapeutic or diagnostic ligand or agent for use with the carrier systems of the present invention will be determined by the nature of the disease, condition, or infection to be assayed and/or treated.

These and more aspects of the invention are disclosed in the following paragraphs.

A. Lipid-Ligand Conjugates

The term "lipid-ligand conjugate" as used herein refers to a compound of the invention, which comprise a linear, bifunctional amino acid at the head group, more specifically a 2-amino-alkanedioic acid (having up to six carbon atoms), such as aspartic acid, glutamic acid, etc., and which are conjugated at coupling sites of the head group to one or more bioactive ligands to form a "lipid-ligand conjugate". The term "ether-lipid (compound)" or "lipid (compound)" as used herein refers to the precursor, i.e. the corresponding lipid prior to conjugation to one or more bioactive ligands.

Thus in one aspect the invention is directed towards lipid-ligand conjugates according to formula I

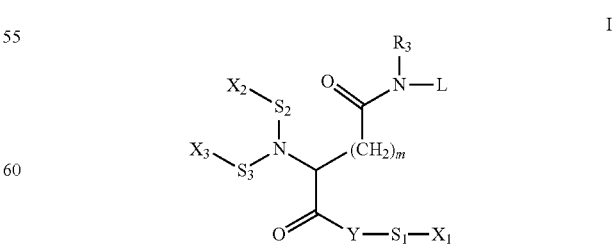

wherein
Y represents O, N, S or a covalent bond,
$S_1$, $S_2$, $S_3$ represent independently of each other a covalent bond or a spacer group, $X_1$, $X_2$, $X_3$ represent independently of each other H or a ligand group, L is a group of formula (a)

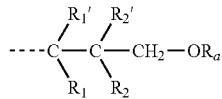
(a)

wherein the dashed line represents the linkage to N,
$R_1$ represents H or a group of formula —$(CH_2)_2$—$OR_{b1}$,
$R_{1'}$ represents H or a group of formula —$(CH_2)_2$—$OR_{b2}$,
$R_2$ represents H or a group of formula —$CH_2$—$OR_c$,
$R_{2'}$ represents H or a group of formula —$OR_d$ or —$CH_2$—$OR_d$,
$R_3$ represents H or a group of formula —$(CH_2)_2$—$OR_e$ or —$(CH_2)_3$—$OR_e$,
$R_a$, $R_{b1}$, $R_{b2}$, $R_c$, $R_d$, $R_e$ represent independently of each other a saturated or unsaturated, straight or branched hydrocarbon chain,
m is 1, 2 or 3,
with the proviso that at least one of $R_1$, $R_{1'}$, $R_2$, $R_{2'}$, $R_3$ is not H and at least one of $X_1$, $X_2$, $X_3$ is a ligand group.

As used herein, the terms "conjugated" (or "conjugation"), "linked", "attached", when used with respect to two or more moieties, refers to physical association of two or more moieties by covalent bonds (either directly or through a spacer).

The corresponding (ether-)lipid compounds which include non-derivatized (lipid) compounds, wherein the headgroup (i.e. the N- and Y-group) do not carry a ligand group but are in free form, in protected form or in activated form), as well as derivatized (lipid) compounds, wherein the headgroup (i.e. the N- and Y-group) is derivatized with one or more spacer groups, are part of an application filed concurrently, which is incorporated herein in its entirety.

In a first embodiment of a compound of I, group $R_3$ is H. More specifically, either (i) $R_3$ is H and $R_1$ and $R_{1'}$ are H, or (ii) $R_3$ is H and $R_2$ and $R_{2'}$ are H. Thus, in this first embodiment the invention is directed towards compounds of formula Ia,

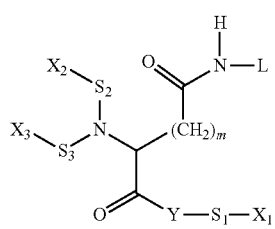
Ia wherein L is a group of formula (a)

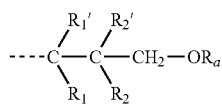
(a)

and wherein $S_1$, $S_2$, $S_3$, $X_1$, $X_2$, $X_3$, Y, $R_1$, $R_{1'}$, $R_2$, $R_{2'}$, $R_a$, and m are defined as above for a compound of formula I.

More specifically, the invention is directed towards compounds of formula Ia, wherein L is a group of formulas (b) or (c)

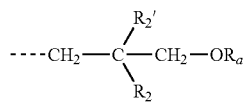
(b)

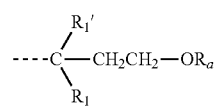
(c)

wherein $R_1$, $R_{1'}$, $R_2$, $R_{2'}$, $R_a$ are defined as above,
with the proviso that in formula (b) one of $R_2$ and $R_{2'}$ is not H, and in formula (c) one of $R_1$ and $R_{1'}$ is not H, and at least one of $X_1$, $X_2$, $X_3$ is a ligand group.

In one preferred embodiment of group (b) $R_2$ is H and $R_{2'}$ is —$OR_d$ or —$CH_2$—$OR_d$. In another preferred embodiment of group (b) $R_2$ is —$CH_2$—$OR_c$ and $R_{2'}$ is —$OR_d$ or $R_{2'}$ is —$CH_2$—$OR_d$.

Thus, the invention is preferably directed to compounds wherein L is a group of formula (b1), (b2), (b3) or (b4):

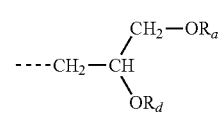
(b1)

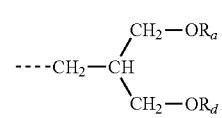
(b2)

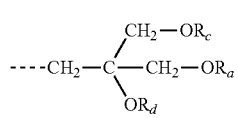
(b3)

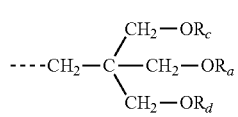
(b4)

wherein $S_1$, $S_2$, $S_3$, $X_1$, $X_2$, $X_3$, Y, m, $R_a$, $R_c$, $R_d$ are defined as above.

In one preferred embodiment of group (c), one of $R_1$ and $R_{1'}$ is H. In another preferred embodiment of group (c) neither of $R_1$ and $R_{1'}$ is H.

Thus, the invention is preferably also directed to compounds wherein L is a group of formula (c1) or (c2):

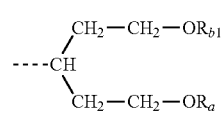
(c1)

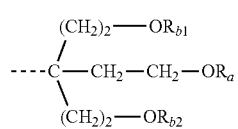
(c2)

wherein $S_1$, $S_2$, $S_3$, $X_1$, $X_2$, $X_3$, Y, m, $R_a$, $R_{b1}$, $R_{b2}$ are defined as above.

In a second embodiment, $R_1$, $R_{1'}$, $R_2$, $R_{2'}$ are H and $R_3$ is either a group of formula —$(CH_2)_2$—$OR_e$ or —$(CH_2)_3$—$OR_e$.

Thus, in this second embodiment the invention is directed towards compounds of formula Ib,

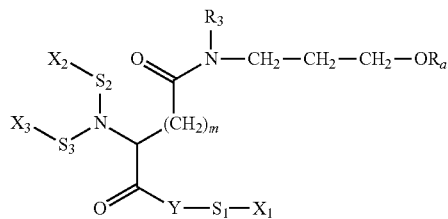

Ib wherein $R_3$ is a group of formula —$(CH_2)_2$—$OR_e$ or —$(CH_2)_3$—$OR_e$, and $S_1$, $S_2$, $S_3$, $X_1$, $X_2$, $X_3$, Y, $R_a$, $R_e$ and m are defined as above.

Most preferred embodiments of the invention are thus compounds of formula I, which are compounds of formulas II or III

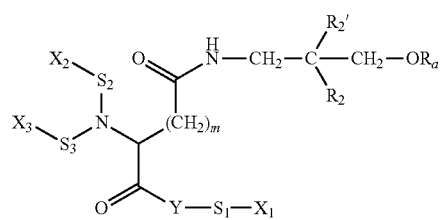

II

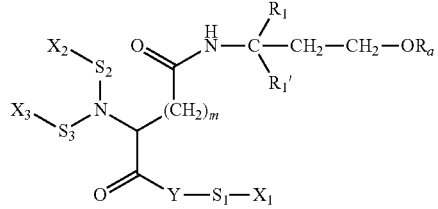

III wherein

Y represents O, N, S or a covalent bond, $S_1$, $S_2$, $S_3$ represent independently of each other a covalent bond or a spacer group, $X_1$, $X_2$, $X_3$ represent independently of each other H or a ligand group, $R_1$ represents H or a group of formula —$(CH_2)_2$—$OR_{b1}$, $R_{1'}$ represents H or a group of formula —$(CH_2)_2$—$OR_{b2}$, $R_2$ represents H or a group of formula —$CH_2$—$OR_c$, $R_{2'}$ represents H or a group of formula —$OR_d$ or —$CH_2$—$OR_d$, $R_a$, $R_{b1}$, $R_{b2}$, $R_c$, $R_d$ represent independently of each other a saturated or unsaturated, straight or branched hydrocarbon chain, m is 1, 2 or 3, with the proviso that (i) in formula II one of $R_2$ and $R_{2'}$ is not H, and in formula III one of $R_1$ and $R_{1'}$ is not H, and that (ii) at least one of $X_1$, $X_2$, $X_3$ is a ligand group.

More specific embodiments of compounds of formula II are compounds of formula IIa, IIb, IIc or IId,

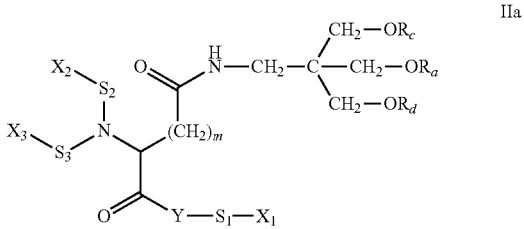

IIa

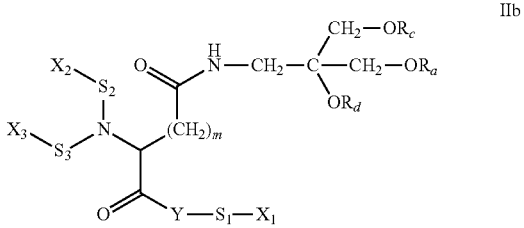

IIb

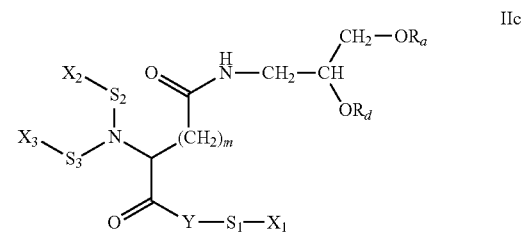

IIc

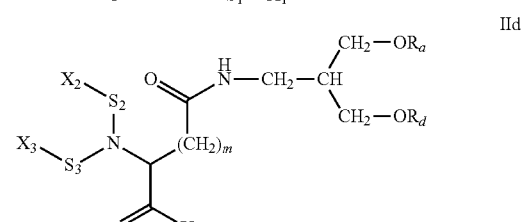

IId wherein $S_1$, $S_2$, $S_3$, $X_1$, $X_2$, $X_3$, Y, $R_a$, $R_c$, $R_d$ and m are defined as above for a compound of formula II.

More specific embodiments of compounds of formula III are compounds of formula IIIa or IIIb,

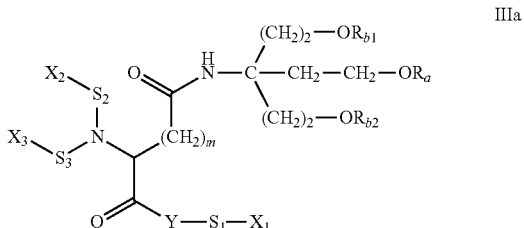

IIIa

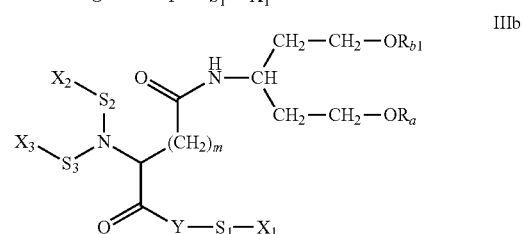

IIIb wherein $S_1$, $S_2$, $S_3$, $X_1$, $X_2$, $X_3$, Y, $R_a$, $R_{b1}$, $R_{b2}$ and m are defined as above for a compound of formula III.

Other most preferred embodiments of compounds of formula I are compounds of formulas IVa and IVb,

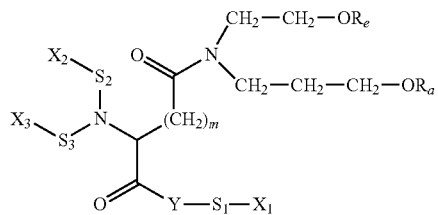

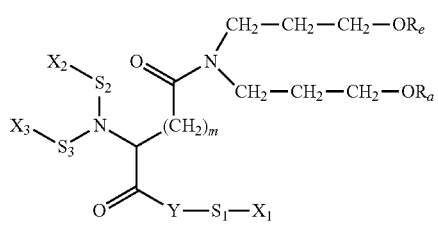

wherein
Y represents O, N, S or a covalent bond,
$S_1$, $S_2$, $S_3$ represent independently of each other a covalent bond or a spacer group,
$X_1$, $X_2$, $X_3$ represent independently of each other H or a ligand group,
$R_a$, $R_e$ represent independently of each other a saturated or unsaturated, straight or branched hydrocarbon chain, and
m is 1, 2 or 3,
with the proviso that at least one of $X_1$, $X_2$, $X_3$ is a ligand group.

A person skilled in the art will appreciate that the ligand-lipid of the present invention (or compounds of the present invention) contain one or more chiral centers and/or double bonds and therefore, may exist as stereoisomers, such as double-bond isomers (i.e., geometric isomers, e.g. Z/E isomers or cis/trans isomers), enantiomers or diastereomers. Accordingly, when stereochemistry at chiral centers is not specified, the chemical structures depicted herein encompass all possible configurations at those chiral centers including the stereoisomerically pure form (e.g., geometrically pure, enantiomerically pure or diastereomerically pure) the enriched form (e.g., geometrically enriched, enantiomerically enriched or diastereomerically enriched) and enantiomeric and stereoisomeric mixtures. The individual isomers may be obtained using the corresponding isomeric forms of the starting material. Alternatively, enantiomeric and stereoisomeric mixtures can be resolved into their component enantiomers or stereoisomers using separation techniques or chiral synthesis techniques well known to the skilled artisan. The compounds of the invention described herein may also exist in several tautomeric forms including the enol form, the keto form and mixtures thereof. Accordingly, the structures depicted herein encompass all possible tautomeric forms of the illustrated compounds.

The term "saturated or unsaturated, straight or branched hydrocarbon chain" as used herein refers to a saturated or unsaturated, straight or branched hydrocarbon chain having 6 to 30, preferably 10 to 22 carbon atoms.

The term "saturated" in combination with hydrocarbon chain refers to a straight or branched alkyl chain, containing 6 to 30, preferably 10 to 22 carbon atoms. Examples include, but are not limited to, capryl (decyl), undecyl, lauryl (dodecyl), myristyl (tetradecyl), cetyl (hexadecyl), stearyl (octadecyl), nonadecyl, arachidyl (eicosyl), heneicosyl, behenyl (docosyl), tricosyl, tetracosyl, pentacosyl, including branched isomers thereof, e.g. isolauryl, anteisolauryl, isomyristyl, anteisomyristyl, isopalmityl, anteisopalmityl, isostearyl, anteisostearyl or phytanyl (3,7,11,15-tetramethylhexadecanyl).

The term "unsaturated" in combination with hydrocarbon chain indicates that fewer than the maximum possible number of hydrogen atoms are bonded to each carbon in the chain giving rise to one or more carbon-carbon double or triple bonds. In preferred embodiments, the number of unsaturated bond(s) in an unsaturated hydrocarbon chain is 1, 2, 3 or 4, preferably 1 or 2.

Examples of alkenyl groups include, but are not limited to, monounsaturated alkenyls, such as decenyl, undecenyl, dodecenyl, palmitoleyl, heptadecenyl, octadecenyl (elaidyl, oleyl, ricinolenyl), nonadecenyl, eicosenyl, heneicosenyl, docosenyl (erucyl), tricosenyl, tetracosenyl, pentacosenyl, and the branched chain isomers thereof, as well as polyunsaturated alkenyls such as octadec-9,12-dienyl (linoleyl, elaidolinoleyl), octadec-9,12,15-trienyl (linolenyl, elaidolinolenyl), 9(Z),11(E),13(E)-octadecatrienyl (eleostearyl), and eicos-5,8,II,14-tetraenyl.

Examples of alkynyl groups include, but are not limited to hexadec-7-ynyl and octadec-9-ynyl.

The term "branched" in combination with hydrocarbon refers to a hydrocarbon chain having a linear series of carbon atoms as a main chain with at least one substituent of one or more carbon atoms as subordinate chain (or branching groups). Examples of subordinate chains include one or more (C1-6)alkyl groups, such as methyl, ethyl, propyl, isopropyl, n-butyl, sec-butyl group, tert-butyl, pentyl, hexyl and the like, one or more (C1-6)alkenyl groups, such as vinyl, allyl, propenyl, isopropenyl, 2-butenyl and the like, or one or more (C1-6)alkynyl groups, such as ethynyl, propynyl, butynyl and the like. Preferred subordinate chains are (C1-6)alkyl groups, most preferred methyl and ethyl.

The compounds of the invention comprise preferably at least two hydrocarbon chains, preferably 2, 3, 4, 5 or 6 hydrocarbon chains, most preferably 2 or 3 hydrocarbon chains, wherein the main chain of the hydrocarbon chains are the same or different, preferably the same, and are selected from an alkyl chain, an alkenyl chain, and an alkynyl chain, preferably an alkyl and an alkenyl chain. In one preferred embodiment, the compounds of the invention carry two alkyl chains, which can be the same or different, preferably the same.

In a specific embodiment of a compound of the invention the hydrocarbon chains $R_a$, $R_{b1}$, $R_{b2}$, $R_c$, $R_d$, $R_e$ are preferably selected from myristyl, palmityl, stearyl, oleyl, linoleyl and phytanoyl.

The terms "alkyl", "alkoxy", "alkenyl", "alkynyl" as used herein have the following meanings:

The term "alkyl refers to a straight or branched alkyl-chain, containing 1 to 12, preferably 1 to 8 carbon atoms. Examples of alkyl groups include, but are not limited to, methyl, ethyl, n-propyl, i-propyl, n-butyl, i-butyl, and t-butyl. The term "alkoxy" refers to an —O-alkyl radical. Examples of alkoxy groups include, but are not limited to, methoxy, ethoxy, and butoxy. The term "alkenyl" refers to a straight or branched unsaturated alkyl group having one or more carbon-carbon double bonds. The above alkyl, alkenyl, and alkoxy groups may be optionally substituted with further groups. Examples of substituents include, but are not limited to, halo, hydroxyl, amino, cyano, nitro, mercapto, alkoxycarbonyl, amido, carboxy, alkylsulfonyl, alkylcarbonyl, carbamido, carbamyl, carboxyl, thioureido, thiocyanato, sulfonamido, aryl, heteroaryl, cyclyl, and heterocyclyl. The term "aryl" refers to an aromatic carbocyclic radical containing about 6 to about 10, preferably 5 to 7 carbon atoms. The aryl group may be optionally substituted with one or more aryl group substituents which may be the same or different, where "aryl group substituent" includes alkyl, alkenyl, alkynyl, aryl, aralkyl, hydroxy, alkoxy, aryloxy, aralkoxy, carboxy, aroyl, halo, nitro, trihalomethyl, cyano, alkoxycarbonyl, aryloxycarbonyl, aralkoxycarbonyl, acyloxy, acylamino, aroylamino, carbamoyl, alkylcarbamoyl, dialkylcarbamoyl, arylthio, alkylthio, alkylene and —NRR', wherein R and R' are each independently hydrogen, alkyl, aryl and aralkyl. Exemplary aryl groups include substituted or unsubstituted phenyl, naphthyl, pyrenyl, anthryl, and phenanthryl.

The term "heteroaryl" refers to an aryl moiety as defined above having at least one heteroatom (e.g., N, O, or S). Examples of a heteroaryl moiety include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl. The term "(hetero)aryloxy" refers to an (hetero)aryl-O-group wherein the (hetero)aryl group is as previously described. Exemplary aryloxy groups include phenoxy and naphthoxy. The term "(hetero)aralkyl" refers to an (hetero)aryl-alkyl-group wherein (hetero)aryl and alkyl are as previously described. Exemplary aralkyl groups include benzyl, phenylethyl and naphthylmethyl. The term "(hetero)aralkyloxy" refers to an (hetero)aralkyl-O-group wherein the (hetero)aralkyl group is as previously described. An exemplary aralkyloxy group is benzyloxy.

The term "cycloalkyl" refers to a saturated or unsaturated, non-aromatic, cyclic hydrocarbon moiety having 6 to 10 carbon atoms, such as cyclohexyl or cyclohexen-3-yl. The term "heterocycloalkyl" refers to a cycloalkyl as defined herein having at least one ring heteroatom (e.g., N, O, or S), such as 4-tetrahydropyranyl or 4-pyranyl.

Aryl, heteroaryl, cycloalkyl, heterocycloalkyl as mentioned herein include both substituted and unsubstituted moieties, unless specified otherwise. Possible substituents on cycloalkyl, heterocycloalkyl, aryl, and heteroaryl include (C1-C10)alkyl, (C2-C10)alkenyl, (C2-C10)alkynyl, (C3-C8)cycloalkyl, (C5-C8)cycloalkenyl, (C1-C10)alkoxy, aryl, aryloxy, heteroaryl, heteroaryloxy, amino, (C1-C10)alkylamino, (C1-C20)dialkylamino, arylamino, diarylamino, hydroxyl, halogen, thio, (C1-C10)alkylthio, arylthio, (C1-C10)alkylsulfonyl, arylsulfonyl, acylamino, aminoacyl, amidino, guanidine, ureido, cyano, nitro, acyl, acyloxy, carboxyl, and carboxylic ester. Cycloalkyl, heterocycloalkyl, aryl, and heteroaryl can also be fused with each other.

Group Y is O, N, S or a covalent linkage, preferably 0 or N, most preferably N. It is understood that if group Y is a covalent linkage, —$S_1$—$X_1$ is directly linked to the CO-group.

The term "spacer" or "spacer group" (or groups $S_1$, $S_2$, $S_3$) as used herein refers to a bivalent branched or unbranched chemical group which allows to link an ether-lipid of the invention to one or more bioactive ligands $X_1$, $X_2$, $X_3$ in sufficient distance to eliminate any undesired interaction between ether-lipid and ligand and/or to reduce any steric hindrance (caused by the ether-lipid itself or any other neighbouring molecules) that may impact the biological activity of the ligand (such as affinity binding of ligands to their target). Depending on the intended use of a conjugate of ether-lipid and bioactive ligand, the spacer groups may be of different length and may be (hydrolytically, enzymatically and chemically) stable or may include a cleavable linkage. Cleavable linkages of the invention may be selected to be cleaved via any form of cleavable chemistry, e.g. chemical, enzymatic, hydrolytic and the like. Exemplary cleavable linkers include, but are not limited to, protease cleavable peptide linkers, nuclease sensitive nucleic acid linkers, lipase sensitive lipid linkers, glycosidase sensitive carbohydrate linkers, pH sensitive linkers, hypoxia sensitive linkers, photo-cleavable linkers, heat-labile linkers, enzyme cleavable linkers, ultrasound-sensitive linkers, x-ray cleavable linkers, etc.

It is understood that the spacers may or may not be end-group activated to allow for linkage of the spacer modified compound of the invention to a further moiety, such as bioactive group.

In specific embodiments, a "spacer group" (or groups $S_1$, $S_2$, $S_3$) represents a short spacer group or a long-chain spacer group selected from an alkylene chain optionally comprising one or more of the groups selected from ketone, ester, ether, amino, amide, amidine, imide, carbamate or thiocarbamate functions, glycerol, urea, thiourea, double bonds or aromatic rings.

More specifically, a short spacer group (or groups $S_1$, $S_2$, $S_3$) may be chosen from (C1-C12)alkyl, (C2-C12)alkenyl, aryl, aralkyl, heteroaryl. A long-chain spacer group (or groups $S_1$, $S_2$, $S_3$) may be chosen from polymeric radicals of formula —W—$(CH_2)_k$—W'—, wherein k is an integer between 13 and 3000, and W and W' are reactive groups able to react with amino, carboxyl, hydroxy or thio groups and wherein one or more of the non-adjacent $CH_2$ groups may independently be replaced by aryl, heteroaryl, —CH=CH—, —C≡C—, or a hydrophilic (or polar) group selected from —O—, —CO—, —CO—O—, —O—CO—, —NR'—, —NR'—CO—, —CO—NR'—, —NR'—CO—O—, —O—CO—NR'—, —NR'—CO—NR'—, and —O—CO—O—, wherein R' represents hydrogen or (C1-C12)alkyl. It is understood that replacing more than one non-adjacent $CH_2$ group by the same group may yield in polymeric chain having a specific repeating unit (e.g. a polyester, polyether, polyimide, etc).

Preferred spacer groups include hydrophilic polymeric radicals (with an increased affinity for aqueous solutions), i.e. polymers containing repeating structural units that comprise one or more of the above hydrophilic (or polar) groups in their alkylene backbone. Typical examples of hydrophilic polymeric radicals include polyoxy($C_2$-$C_3$)alkylenes (e.g. polyethylene glycol (PEG) or polypropylene glycol (PPG)), polysaccharides (e.g. dextran, pullulan, chitosan, hyaluronic acid), polyamides (e.g. polyamino acids, semisynthetic peptides and polynucleotides); polysialic acid, polyesters (e.g. polylactide (PLA), polylactid-co-glycolid (PLGA)), polycarbonates, polyethyleneimines (PEI), polyimides polyvinyl acetate (PVA).

A preferred spacer is "PEG" or "polyethylene glycol", which encompasses any water-soluble poly(ethylene oxide). Typically, "PEG" means a polymer that contains a majority, e.g. >50%, of subunits that are —$CH_2CH_2O$—. Different forms of PEG may differ in molecular weights, structures or geometries (e.g., branched, linear, forked PEGs, multifunctional, and the like). PEGs for use in the present invention may preferably comprise one of the two following structures: "—$O(CH_2CH_2O)_m$—" or "—$CH_2CH_2O(CH_2CH_2O)_m$—$CH_2CH_2$—," where m is 3 to 3000, and the terminal groups and architecture of the overall PEG may vary. As indicated above, depending on its use, PEG may be in end-capped form.

When PEG is defined as "—$O(CH_2CH_2O)_m$—" the end capping group is generally a carbon-containing group typically comprised of 1-20 carbons and is preferably alkyl (e.g., methyl, ethyl or benzyl) although saturated and unsaturated forms thereof, as well as aryl, heteroaryl, cyclyl, heterocyclyl, and substituted forms of any of the foregoing are also envisioned. When PEG is defined as "—$CH_2CH_2O(CH_2CH_2O)_m$—$CH_2CH_2$—", the end capping group is generally a carbon-containing group typically comprised of 1-20 carbon atoms and an oxygen atom that is covalently bonded to the group and is available for covalently bonding to one terminus of the PEG. In this case, the group is typically alkoxy (e.g., methoxy, ethoxy or benzyloxy) and with respect to the carbon-containing group can optionally be saturated and unsaturated, as well as aryl, heteroaryl, cyclyl, heterocyclyl, and substituted forms of any of the foregoing. The other ("non-end-capped") terminus is typically a hydroxyl, amine or an activated group that can be subjected to further chemical modification when PEG is defined as "—$CH_2CH_2O(CH_2CH_2O)_m$—$CH_2CH_2$—" In addition, the end-capping group can also be a silane.

A review for the preparation of various end-group functionalized or activated PEG is known in the art (see for example Zalipsky S., Bioconjug. Chem., 6, 150-165 (1995)).

Methods for conjugating a bioactive ligand ($X_1$ and/or $X_2$ and/or $X_3$) to an ether-lipid (i.e. compounds of formula I wherein $X_1$, $X_2$, $X_3$ are H) include covalent binding of one or more bioactive ligands $X_1$, $X_2$, $X_3$ to one or more of the reactive positions at the head group (i.e. N- and/or Y-group) of one or more individual ether-lipid. Thus, one bioactive ligand may be attached to one or more sites of one individual ether-lipid or to more than one site of more than one individual ether-lipid. Alternatively, two or three bioactive ligands are attached to the coupling sites of one individual ether-lipid. The one or more bioactive groups maybe attached directly to the ether-lipid or via a spacer group.

Typically, methods for linking may generally include the steps of:
a) providing a lipid compound of formula I, wherein $X_1$, $X_2$, $X_3$ are H, carrying one or more coupling sites on one or more of groups $S_1$, $S_2$, $S_3$,
b) providing an antigen ligand carrying a reactive group suitable for reacting with the one or more coupling sites, and
c) reacting the lipid compound with the antigen to obtain a ligand-lipid conjugate.

The term "coupling site" or "coupling group", as used herein, refers to a reactive or functional group capable of reacting with a corresponding reactive or functional group (or two coupling partners) in a coupling reaction to form a covalent bond (C—C, C—O, C—N, C—S-linkage). The choice of conjugation (or coupling) method depends on various factors, such as the nature of the bioactive ligand to be attached, i.e. physical attributes (e.g. size, charge, etc.), the nature of the reactive groups present on the bioactive ligand, and the like.

In some embodiments, conjugation is carried out in the presence of a bifunctional agent (i.e., an agent with two functional (end)groups), preferably a heterobifunctional agent (i.e., an agent with two different functional (end) groups). The use of such a (hetero)bifunctional agent results in a lipid-ligand conjugate wherein lipid and ligand may be directly linked to each other or separated by a spacer. Typical functional groups include, but are not limited to, groups such as succinimidyl esters, maleimides, and pyridyldisulfides. In some embodiments, the bifunctional agent is selected from, but not limited to, e.g., carbodiimides, N-hydroxysuccinimidyl-4-azidosalicylic acid (NHS-ASA), dimethyl pimelimidate dihydrochloride (DMP), dimethylsuberimidate (DMS), 3,3'-dithiobispropionimidate (DTBP), N-Succinimidyl 3-[2-pyridyldithio]-propionamido (SPDP), succinimidyl α-methylbutanoate, biotinamidohexanoyl-6-amino-hexanoic acid N-hydroxy-succinimide ester (SMCC), succinimidyl-[(N-maleimidopropionamido)-dodecaethyleneglycol]ester (NH S-PEO12), N-succinimidyl (4-iodoacetyl) aminobenzoate (SIAB), N-succinimidyl S-acetylthioacetate (SATA), m-maleimidobenzoyl-N-hydroxysuccinimide ester (MBS) and N-□-maleimidobutyryloxy-succinimide ester (GMBS), succinmidyl dicarbonyl pentane or disuccinimidyl suberate. In other embodiments, the bifunctional agent is Traut's Reagent 2-iminothiolane in combination with SPDP. In still a further embodiment the linker is. In a further embodiment, the bifunctional agent is selected among those disclosed in The Pierce Products Catalogue (Pierce Chemical Company, USA) and the Double Agents™ Cross-Linking Reagents Selection Guide (Pierce Chemical Company), which are herein incorporated by reference.

Preferred conjugation methods include carbodiimide-mediated amide formation and active ester maleimide-mediated amine and sulfhydryl coupling, and the like.

For example, a thiol-containing molecule may be reacted with an amine-containing molecule using a heterobifunctional cross-linking reagent, e.g., a reagent containing both a succinimidyl ester and either a maleimide, a pyridyldisulfide, or an iodoacetamide. Amine-carboxylic acid and thiol-carboxylic acid cross-linking, maleimide-sulfhydryl coupling chemistries (e.g., the maleimidobenzoyl-N-hydroxysuccinimide ester (MBS) method), etc., may be used.

Polypeptides can conveniently be conjugated to an ether-lipid via amine or thiol groups in lysine or cysteine side chains respectively, or by an N-terminal amino group. Likewise, oligonucleotides can conveniently be conjugated to an etherlipid through a unique reactive group on the 3' or 5' end, e.g. a sulfhydryl, amino, phosphate group or the like. Reactive sulfhydryl groups may be coupled to a lipid of formula I having a free amino group (e.g. groups N and Y) through the use of reagents such as (i) N-succinimidyl 3-(2-pyridyldithio)propionate (SPDP) and long chain SPDP (lc-SPDP) yielding a cleavable disulfide bond between the lipid and the oligonucleotide or polypeptide, or (ii) succinimidyl-iodoacetate to produce non-cleavable bonds between the lipid and oligonucleotide or polypeptide. These and other conjugation techniques are known in the art (see e.g. U.S. Pat. No. 5,512,439; WO 01/22995; Greg Hernanson "Bioconjugate Techniques," Academic Press, 1996; Gordon Bickerstaff "Immobilization of Enzymes and Cells," Humana Press, 1997).

A skilled person will know which functional group or functional groups (e.g., amine, carbonyl or carboxyl groups on the spacer group $S_1$, $S_2$, $S_3$ of the headgroup of an ether-lipid of formula I to choose to allow conjugation to occur with a bioactive ligand according to the above described conjugation methods.

Additional general information on conjugation methods can be found e.g. in "Cross-Linking," Pierce Chemical Technical Library, available at the Pierce web site and originally published in the 1994-95 Pierce Catalog, and references cited therein; Wong SS, Chemistry of Protein Conjugation and Cross-linking, CRC Press Publishers, Boca Raton, 1991; and Hermanson, G. T., Bioconjugate Techniques, Academic Press, Inc., San Diego, 1996.

Molar ratios to be used in conjugating one or more ligands to an ether-lipid compound of formula I may be readily optimized by a skilled person. Typically, it may range from about 1:1 to about 10:1 lipid compound to ligand.

In the general method presented above, any suitable method may be used to purify an intermediate conjugated compound, such as by preparative reverse phase HPLC (RP-HPLC), by membrane filtration, such as ultrafiltration or diafiltration. Unreacted reactants may be removed by size exclusion chromatography, such as gel filtration, or equilibrium dialysis. The final conjugate may also be purified using any suitable means, including for instance gel filtration, membrane filtration, such as ultrafiltration, or ion exchange chromatography, or a combination thereof. The lipid-ligand conjugates of the invention are particularly suitable for use in the preparation of lipidic or nanoparticulate carrier systems, such as liposomes, micelles and nanoparticles.

B. Lipidic Carrier Systems

In a further aspect the invention is directed to a lipidic carrier system comprising one or more lipid-ligand conjugates of the invention optionally in combination with other co-lipids.

Exemplary lipidic carrier systems preferably include lipid(ic) vesicles. The term "lipid(ic) vesicle" (or present vesicles or vesicles of the invention) is used interchangeably with the expression lipidic carrier systems and refers to a spherical entity which is characterized by the presence of an internal void. Typically, vesicles of the invention are formed from one or more lipid-ligand conjugates optionally in combination with other synthetic or naturally-occurring lipids (co-lipids). In any given vesicle of the invention, the lipids may be in the form of a monolayer or a bilayer. In the case of more than one mono- or bilayer, the mono- or bilayers are generally concentric. The present vesicles include such entities commonly referred to as liposomes (i.e. a vesicle including one or more concentrically ordered lipid bilayer(s) with an internal void), micelles (i.e. a vesicle including a single lipid monolayer with an internal void), and the like. Thus, the lipids may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers).

The internal void of the vesicles are generally filled with a liquid, including, for example, an aqueous liquid, a gas, a gaseous precursor, and/or a solid material, including, for example, one or more bioactive agents, see also hereinafter.

In some embodiments the ligand of the lipid-ligand conjugate is a targeting ligand (to yield a targeted lipidic carrier system or targeted liposome). In other embodiments the ligand of the lipid-ligand conjugate is an antigenic ligand (to yield an antigenic lipidic carrier system or antigenic liposome).

Thus the present invention is specifically directed towards a targeted lipid vesicles (such as a targeted liposome or micelle), comprising a lipid-ligand conjugate of formula I, wherein one or more of groups $X_1$, $X_2$, $X_3$ are a targeting ligand, optionally in combination with other co-lipids. Alternatively, the present invention is specifically directed towards an antigenic lipid vesicles (such as an antigenic liposome or micelle), comprising a lipid-ligand conjugate of formula I, wherein one or more of groups $X_1$, $X_2$, $X_3$ are an antigenic ligand, optionally in combination with other co-lipids.

In specific embodiments the present invention is also directed towards a mixed lipid vesicles (such as a mixed liposome or micelle), comprising a lipid-ligand conjugate of formula I, wherein one or more of groups $X_1$, $X_2$, $X_3$ are an antigenic ligand and a targeting ligand, optionally in combination with other co-lipids.

In specific embodiments the lipid vesicles of the invention (i.e. targeted, antigenic or mixed) further comprise one or more bioactive agents, such as a therapeutic or a diagnostic or an antigenic agent, preferably a therapeutic or a diagnostic agent, either (a) enclosed within the internal void of the lipid vesicles of the invention, (b) integrated within the layer(s) or wall(s) of the lipid vesicles of the invention, for example, by being interspersed among lipids which are contained within the layer(s) or wall(s) of the lipid vesicles of the invention, or (c) exposed on the surface of the lipid vesicles of the invention, whereby the surface exposure is achieved through various chemical interactions, such as electrostatic interactions, hydrogen bonding, van der Waal's forces or covalent bonding resulting in attachment or adsorption and the like.

A skilled person will understand that all combinations are contemplated within this invention, such as a targeted lipid vesicle comprising an enclosed antigenic agent, etc.

In specific embodiments the lipid vesicles of the invention comprising an antigenic ligand and/or agent may further comprise one or more, preferably one adjuvant either (a) enclosed within the internal void of said lipid vesicles, (b) integrated within the layer(s) or wall(s) of said lipid vesicles, for example, by being interspersed among lipids which are contained within the layer(s) or wall(s) of said lipid vesicles, or (c) exposed on the surface of said lipid vesicles, whereby its surface exposure is achieved through various chemical interactions, such as electrostatic interactions, hydrogen bonding, van der Waal's forces or covalent bonding.

Preferably, the one or more adjuvants are enclosed within the internal void.

The term "co-lipid" or "vesicle-forming (co-)lipid" as used herein refers to lipids which may optionally be present as additional lipids in the lipid vesicles of the invention and may include acyclic and cyclic, saturated or unsaturated lipids of natural or synthetic origin. As used herein a co-lipid may be a neutral lipid, a cationic lipid or an anionic lipid. A cationic lipid has a positive net charge and may include lipids such as N-[1-(2,3-dioleoyloxy)propyl]-N,N,N-trimethyl ammonium salts, e.g. the methylsulfate (DOTAP), DDAB, dimethyldioctadecyl ammonium bromide; 1,2-diacyloxy-3-trimethylammonium propanes, (including but not limited to: dioleoyl, dimyristoyl, dilauroyl, dipalmitoyl and distearoyl; also two different acyl chain can be linked to the glycerol backbone); N-[1-(2,3-dioloyloxy)propyl]-N,N-dimethyl amine (DODAP); 1,2-diacyloxy-3-dimethylammonium propanes, (including but not limited to: dioleoyl, dimyristoyl, dilauroyl, dipalmitoyl and distearoyl; also two different acyl chain can be linked to the glycerol backbone); N-[1-(2,3-dioleyloxy)propyl]-N,N,N-trimethylammonium chloride (DOTMA); 1,2-dialkyloxy-3-dimethylammonium propanes, (including but not limited to: dioleyl, dimyristyl, dilauryl, dipalmityl and distearyl; also two different alkyl chain can be linked to the glycerol backbone); dioctadecylamidoglycylspermine (DOGS); 3β-[N—(N',N'-dimethylamino-ethane)carbamoyl]cholesterol (DC-Chol); 2,3-dioleoyloxy-N-(2-(sperminecarboxamido)-ethyl)-N,N-dimethyl-1-propanam-inium trifluoro-acetate (DOSPA); β-alanyl cholesterol; cetyl trimethyl ammonium bromide (CTAB); diC14-amidine; N-tert-butyl-N'-tetradecyl-3-tetradecylamino-propionamidine; 14Dea2; N-(alpha-trimethylammonioacetyl)didodecyl-D-glutamate chloride (TMAG); O,O'-ditetradecanoyl-N-(trimethylammonio-acetyl)diethanolamine chloride; 1,3-dioleoyloxy-2-(6-carboxy-spermyl)-propylamide (DOSPER); N,N,N',N'-tetramethyl-N,N'-bis(2-hydroxyethyl)-2,3-dioleoyloxy-1,4-butan-ediammonium iodide; 1-[2-(acyloxy)ethyl]2-alkyl(alkenyl)-3-(2-hydroxyethyl)-imidazolinium chloride derivatives (as described by Solodin et al. (1995) Biochem. 43:13537-13544), such as 1-[2-(9(Z)-octadecenoyloxy)ethyl]-2-(8(Z)-heptadecenyl-3-(2-hydroxyethyl) imidazolinium chloride (DOTIM), 1-[2-

(hexadecanoyloxy)ethyl]-2-pentadecyl-3-(2-hydroxyethyl) imidazolinium chloride (DPTIM), 2,3-dialkyloxypropyl quaternary ammonium compound derivatives, containing a hydroxyalkyl moiety on the quaternary amine (see e.g. by Feigner et al. J. Biol. Chem. 1994, 269, 2550-2561), such as: 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimethyl-hydroxypropyl ammonium bromide (DORIE-HP), 1,2-dioleyloxypropyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxylethyl ammonium bromide (DMRIE), 1,2-dipalmityloxypropyl-3-dimethyl-hydroxyethyl ammonium bromide (DPRIE), 1,2-distery-loxypropyl-3-dimethyl-hydroxyethyl ammonium bromide (DSRIE); cationic esters of acyl carnitines (as reported by Santaniello et al. U.S. Pat. No. 5,498,633); cationic triesters of phospahtidylcholine, i.e. 1,2-diacyl-sn-glycerol-3-ethylphosphocholines, where the hydrocarbon chains can be saturated or unsaturated and branched or non-branched with a chain length from $C_{12}$ to $C_{24}$, the two acyl chains being not necessarily identical. Neutral or anionic lipids have a neutral or anionic net charge, respectively. These can be selected from sterols or lipids such as cholesterol, phospholipids, lysolipids, lysophospholipids, sphingolipids or pegylated lipids with a neutral or negative net change. Useful neutral and anionic lipids thereby include: phosphatidylserine, phosphatidylglycerol, phosphatidylinositol (not limited to a specific sugar), fatty acids, sterols, containing a carboxylic acid group for example, cholesterol, cholesterol sulfate and cholesterol hemisuccinate, 1,2-diacyl-sn-glycero-3-phosphoethanolamine, including, but not limited to, DOPE, 1,2-diacyl-glycero-3-phosphocholines and sphingomyelin. The fatty acids linked to the glycerol backbone are not limited to a specific length or number of double bonds. Phospholipids may also have two different fatty acids.

A skilled person will understand that the ratio of lipid-ligand conjugates to co-lipids depends on the nature of the bioactive ligand, the nature of the optional bioactive agent enclosed or embedded within or adsorbed onto or attached to the lipid vesicles, the intended use (treatment of disease, diagnostic assay, etc.), the formulation as pharmaceutical composition and the route of administration.

In one embodiment a lipid vesicle of the invention may comprise lipid-ligand conjugates of the invention and other vesicle-forming lipids (co-lipids) preferably in a ratio from 1:1'000 to 1:1, preferably 1:500 to 1:50. In further embodiments of the invention, the lipid vesicles may comprises one or more lipid-ligand conjugates wherein the ether-lipid of the conjugate comprises unsaturated hydrocarbon chains, which may be crosslinked or polymerized to form polymerized lipid vesicles.

As used herein, the term "polymerized lipid vesicles" and (in particular a polymerized liposome) means a lipid vesicle in which the constituent lipids are covalently bonded to each other by intermolecular interactions. The lipids can be bound together within a single layer of the lipid bilayer (the leaflets) and/or bound together between the two layers of the bilayer. Polymerizing the lipid layer structure makes the assembly dramatically more resistant to enzymatic breakdown by acids, bile salts or enzymes present in vivo. In addition, controlling the degree of polymerization and the degradation rate (by choosing specific ratios of lipid-ligand conjugates having cleavable or polymerizable hydrocarbon chains), the stability as well as "leakiness" (by generating pores of a desired size) can be tuned according to the desired escape rate of an optionally enclosed bioactive agent. Thus the design of a lipid vesicle allows modulating the optimal escape rate of e.g. any encapsulated antigen agent at specific immune uptake sites, or any encapsulated therapeutic agent at specific tissue or cell sites, etc.

As those skilled in the art will recognize, lipidic carrier systems in form of vesicles such as liposomes, micelles, or other vesicles, may be readily prepared from lipid-ligand conjugates of the invention using standard conditions known in the art.

Depending on the desired physical properties, lipid vesicles may be prepared from lipid-ligand conjugates optionally in combination with one or more co-lipids including stabilizing lipids. The particular stabilizing compounds which are ultimately combined with the present lipid-ligand conjugates may be selected as desired to optimize the properties of the resulting lipid vesicles (and are readily identifiable by one skilled in the art without undue experimentation).

Micellar compositions according to the invention may be prepared using any one of a variety of conventional micellar preparatory methods which will be apparent to those skilled in the art. These methods typically involve suspension of a lipid-ligand conjugate in an organic solvent, evaporation of the solvent, resuspension in an aqueous medium, sonication and centrifugation. The foregoing methods, as well as others, are discussed, for example, in Canfield et al., Methods in Enzymology, Vol. 189, pp. 418-422 (1990); El-Gorab et al, Biochem. Biophys. Acta, Vol. 306, pp. 58-66 (1973); Colloidal Surfactant, Shinoda, et al, Academic Press, N.Y. (1963) (especially "The Formation of Micelles", Shinoda, Chapter 1, pp. 1-88); Catalysis in Micellar and Macromolecular Systems, Fendler and Fendler, Academic Press, N.Y. (1975). The disclosures of each of the foregoing publications are incorporated by reference herein, in their entirety. Optional stabilizing materials be combined with the lipid-ligand conjugates to stabilize the micellar compositions produced therefrom include lauryltrimethylammonium bromide, cetyltrimethylammonium bromide, myristyltrimethyl-ammonium bromide, (C12-C16)alkyldimethylbenzylammonium chloride, cetylpyridinium bromide and chloride, lauryl sulphate, and the like. Other materials for stabilizing the micellar compositions, in addition to those exemplified above, would be apparent to one skilled in the art based on the present disclosure. Liposomal compositions of the invention are particularly preferred as they are particularly effective as carriers for the delivery of bioactive agents to tissues and cells or as antigen presenting carriers.

Liposomal compositions may comprise one or more lipid-ligand conjugates optionally in combination with one or more further co-lipids and/or one or more stabilizing compounds. The lipid-ligand conjugates (and co-lipids) may be in the form of a monolayer or bilayer, and the mono- or bilayer lipids may be used to form one or more mono- or bilayers. In the case of more than one mono- or bilayer, the mono- or bilayers are generally concentric. Thus, the lipid-ligand conjugates (and co-lipids) may be used to form a unilamellar liposome (comprised of one monolayer or bilayer), an oligolamellar liposome (comprised of two or three monolayers or bilayers) or a multilamellar liposome (comprised of more than three monolayers or bilayers).

The selection of suitable co-lipids and stabilizing compounds in the preparation of liposomal lipid compositions of the invention would be apparent to a person skilled in the art and can be achieved without undue experimentation, based on the present disclosure.

Other materials for use in the preparation of liposomal lipid compositions of the invention, in addition to those exemplified above, would be apparent to one skilled in the art based on the present disclosure.

The amount of stabilizing material, such as, for example, additional amphipathic compound, which is combined with the present lipid-ligand conjugates may vary depending upon a variety of factors, including the specific lipid-ligand conjugate(s) of the invention selected, the specific stabilizing material(s) selected, the particular use for which it is being employed, the mode of delivery, and the like. The amount of stabilizing material to be combined with the present lipid-ligand conjugates and the ratio of stabilizing material to lipid-ligand conjugates, will vary and is readily determinable by one skilled in the art based on the present disclosure. Typically ratios higher than about 4:1, 3:1 or 2:1, of lipid-ligand conjugate to stabilizing lipid, are preferred.

A wide variety of methods are available in connection with the preparation of liposomal compositions of the invention. Accordingly, the liposomes may be prepared using any one of a variety of conventional liposome preparatory techniques which will be apparent to those skilled in the art. These techniques include ethanol injection, thin film technique, homogenizing, solvent dialysis, forced hydration, reverse phase evaporation, microemulsification and simple freeze-thawing, Using e.g. conventional microemulsification equipment. Additional methods for the preparation of liposomal compositions of the invention from the lipid-ligand conjugates of the present invention include, for example, sonication, chelate dialysis, homogenization, solvent infusion, spontaneous formation, solvent vaporization, controlled detergent dialysis, and others, each involving the preparation of liposomes in various ways. Typically, methods which involve ethanol injection, thin film technique, homogenizing and extrusion are preferred in connection with the preparation of liposomal compositions of the invention from the lipid-ligand conjugates of the present invention.

The size of the liposomes can be adjusted, if desired, by a variety of techniques, including extrusion, filtration, sonication and homogenization. Other methods for adjusting the size of the liposomes and for modulating the resultant liposomal biodistribution and clearance of the liposomes would be apparent to one skilled in the art based on the present disclosure. Preferably, the size of the liposomes is adjusted by extrusion under pressure through pores of a defined size. The liposomal compositions of the invention may be of any size, preferably less than about 200 nanometer (nm) in outside diameter.

As those skilled in the art will recognize, any of the lipid-ligand conjugates and lipidic carrier systems comprising the lipid-ligand conjugates of the invention may be lyophilized for storage, and reconstituted in, for example, an aqueous medium (such as sterile water or phosphate buffered solution, or aqueous saline solution), preferably under vigorous agitation. If necessary, additives may be included to prevent agglutination or fusion of the lipids as a result of lyophilisation. Useful additives include, without limitation, sorbitol, mannitol, sodium chloride, glucose, trehalose, polyvinylpyrrolidone and poly(ethylene glycol), for example, PEG 400.

C. Nanoparticulate Carrier Systems

Nanoparticulate carrier systems may exist in any shape and any morphology. Examples of nanoparticulate carrier systems include nanoparticles, nanopowders, nanoclusters, nanocrystals, nanospheres, nanofibers, nanotubes and other geometries. Nanoparticulate vesicular compositions or nanoparticles are typically small particles having typically a diameter of less than 1 micron, preferably in the range of about 25-1000 nm, more preferably in the range of about 50-300 nm, most preferably in the range of about 60-200 nm. A nanosphere refers to a type of nanoparticle that is approximately spherical in shape and has a hollow core. Typically, nanoparticles have a matrix core structure which may be formed using all types of materials and structures, including inorganic materials, such as metals, and organic materials, such as polymers including physiologically acceptable polymers. Non-limiting examples of such polymers include, for example, polyesters (such as poly(lactic acid), poly(L-lysine), poly(glycolic acid) and poly(lactic-co-glycolic acid)), poly(lactic acid-co-lysine), poly(lactic acid-graft-lysine), polyanhydrides (such as poly(fatty acid dimer), poly(fumaric acid), poly(sebacic acid), poly(carboxyphenoxy propane), poly(carboxyphenoxy hexane), copolymers of these monomers and the like), poly(anhydride-co-imides), poly(amides), poly(orthoesters), poly(iminocarbonates), poly(urethanes), poly(organophasphazenes), poly(phosphates), poly(ethylene vinyl acetate) and other acyl substituted cellulose acetates and derivatives thereof, poly(caprolactone), poly(carbonates), poly(amino acids), poly(acrylates), polyacetals, poly(cyanoacrylates), poly(styrenes), poly(vinyl chloride), polyvinyl fluoride), polyvinyl imidazole), chlorosulfonated polyolefins, polyethylene oxide, copolymers, polystyrene, and blends or co-polymers thereof. The nanoparticles may also include hydroxypropyl cellulose (HPC), N-isopropylacrylamide (NIPA), polyethylene glycol, polyvinyl alcohol (PVA), polyethylenimine, chitosan, chitin, dextran sulfate, heparin, chondroitin sulfate, gelatin, etc. as well as their derivatives, co-polymers, and mixtures thereof. A non-limiting method for making nanoparticles is described e.g. in U.S. Publication 2003/0138490. In another embodiment the core material may be selected from metals, alloys, metalloids, metal compounds such as metal oxides, inorganic compounds, and carbon-based materials, in particular carbon nanotubes, one-dimensional nanoparticles of fullerene $C_{60}$, and three-dimensional nanoparticles of fullerene $C_{70}$. Suitable examples of metals include, but are not limited to, noble or a platinum metal such as Ag, Au, Pd, Pt, Rh, Ir, Ru, and Os, transition metals such as Ti, Cr, Mn, Fe, Co, Ni, Cu, Zn, Zr, Nb, Mo, Ta, W, Re, and main group metals such as Al, Ga, In, Si, Ge, Sn, Sb, Bi, Te. It will be appreciated that some main group metals, in particular Si and Ge, are also commonly referred to as metalloids. Suitable examples of alloys include, but are not limited to, alloys of noble or platinum metal and transition metals, in particular alloys of silver and transition metals such as Ag/Ni, Ag/Cu, Ag/Co, and platinum and transition metals such as Pt/Cu, or noble or platinum alloys such as Ru/Pt. Non-limiting examples of inorganic compounds include, but are not limited, to $SiO_2$, metal compounds, in particular metal oxides such as $TiO_2$ and iron oxides. Nanoparticles may also comprise intrinsic fluorescent or luminescent moieties, plasmon resonant moieties, and magnetic moieties, which provide such nanoparticles with detectable electrical, magnetic, and/or optical properties.

A skilled person will know that the choice of material may depend on the intended use of the nanoparticle.

In one embodiment, the invention is directed towards a nanoparticle comprising one or more lipid-ligand conjugates. The one or more lipid conjugates may be entangled, embedded, incorporated, encapsulated, adsorbed or bound to the surface, or otherwise associated with the nanoparticle.

In one specific embodiment the lipid-ligand conjugate may be associated to a nanoparticle in form of a coating, through intermolecular forces such as Van-der-Waals forces, ionic interactions, hydrophobic interactions, optionally in combination with other co-lipids.

Alternatively, nanoparticles may optionally include one or more functional groups, such as, for example, a carboxyl, sulhydryl, hydroxyl, or amino group, for covalently linking one or more lipid-ligand conjugates (or other compounds, such as spacers) to the surface of the nanoparticles, optionally in combination with other co-lipids.

Nanoparticles of the invention may also be grouped together (optionally with a dispersing agent) to form a nanocluster. The independent formulation of each nanoparticle type before cluster formation and a special arrangement of nanoparticles within the cluster may allow controlling the retention and concentration of a lipid-ligand conjugate and thus of the bioactive agent.

In some embodiments, the nanoparticles may further comprise an additional bioactive agent entrapped, embedded, or encapsulated within the solid matrix core of the nanoparticle.

In preferred embodiments, the lipid-ligand coated nanoparticles may be formed from nanosized core particles and one or more lipid-ligand conjugates of the present invention and optionally one or more co-lipids. In any given lipid-ligand coated nanoparticle, the lipid-ligand conjugates may be in the form of a monolayer or a bilayer. In the case of more than one mono- or bilayer, the mono- or bilayers are generally concentric. Coating of the nanoparticles is preferably carried out in a solution comprising the lipid-ligand conjugates of the invention and by allowing sufficient time to allow the lipid-ligand conjugates to coat the nanoparticles.

In some embodiments, the one or more ligands of the one or more lipid-ligand conjugates are one or more antigenic ligands.

The amount of antigenic ligand per nanoparticle (or surface density of the antigenic ligand) to induce an immune response depends on many factors, such as the nature of the immune response itself (humoral vs. cell-mediated), the immunogenicity of the antigen ligand, the immunogenic constitution of the challenged organism, and the administration route and duration of exposure to the antigen. Clearly, immunization of a subject may be enhanced by the use of multiple copies of an antigen as a multivalent display thereby increasing site-specifically antigen concentration and thus inducing a long-lasting immune responses. It is particularly desirable in case of antigen ligands such as small peptides or carbohydrates, that are difficult to administer and generally fail to elicit an effective immune response due to the hapten-related size issues.

Thus, in some embodiments the nanoparticle displays single or multiple copies of one antigen ligand or a combination of different antigen ligands on its surface (in form of a multivalent display). As used herein, the term "multivalent" refers to the display of more than one copy or type of antigen on a carrier system.

More specifically, the present invention relates to a nanoparticle comprising a solid core which is coated by at least one lipid-ligand conjugate of formula I, wherein one or more of $X_1$, $X_2$, $X_3$ are an antigenic ligand, and optionally other matrix or co-lipids.

Immunization may be further improved by including targeting ligands to direct the nanoparticle to the appropriate immune cell or location. Compounds which may act as targeting ligands are compounds that interfere with the adherence of pathogens to host cells and thus successful colonization. Examples of such compounds may include the tetanus toxoid; P pili of *E. coli*; type IV pili of *Pseudomonas aeruginosa*, *Neisseria species*, *Moraxella species*, EPEC, or *Vibrio cholerae*; fimbrial genes and several a fimbrial adhesins, including FHA, pertactin, pertussis toxinand BrkA of *Bordetella pertussis*; and SipB-D of *Salmonella typhimurium*; and the adenovirus adhesion; the Reovirus sigma-1 protein which targets the M-cell.

Thus, the invention also refers to a nanoparticle comprising a solid core which is coated by at least one lipid-ligand conjugate of formula I, wherein one or more of $X_1$, $X_2$, $X_3$ are an antigenic ligand and/or a targeting ligand, and optionally other matrix or co-lipids.

In other embodiments a lipid-ligand coated nanoparticle further comprises a single antigenic agent or a combination of antigenic agents (multivalent) enclosed or embedded within the solid core of the nanoparticle. Thus, the invention also refers to a nanoparticle comprising a solid core, which is coated by at least one lipid-ligand conjugate of formula I, wherein one or more of $X_1$, $X_2$, $X_3$ are an antigenic ligand and/or a targeting ligand, and optionally other matrix or co-lipids, and wherein the solid core optionally comprises one or more further antigenic agents.

In yet other embodiments the nanoparticle further comprises one or more adjuvants enclosed, embedded or dispersed within the solid core of the nanoparticle.

As used herein the term "adjuvant" refers to any material capable of enhancing a humoral and/or cellular immune response to a specific antigen. Suitable adjuvants may be displayed on the surface of a nanoparticle, intercalated into a nanoparticle wall or encapsulated into a nanoparticle interior. Examples of adjuvants that may be used to promote the production of serum and/or mucosal antibodies as well as cell-mediated immune responses against co-administered antigens include *E. coli* heat-labile enterotoxin holotoxin (LT) and *Vibrio cholerae* enterotoxin (CT) as well as the KPL adjuvant (derived from the cell wall of *Salmonella Minnesota*).

As used herein, the terms "displayed" or "surface exposed" refer to any ligand that is present at the external surface of a carrier system such as a lipidic vesicle or a nanoparticle and thus is accessible for recognition. A variety of diseases and disorders may be treated by such nanoparticle vaccine constructs or assemblies, including: inflammatory diseases, infectious diseases, cancer, genetic disorders, organ transplant rejection, autoimmune diseases and immunological disorders.

Thus the invention also encompasses a vaccine comprising multivalent nanoparticles comprising a solid core and one or more surface exposed lipid-ligand conjugates, wherein the ligand is one or more antigenic and/or targeting ligands, further optionally comprising an adjuvant and/or a further antigenic agent embedded in the solid core of the nanoparticles. In further embodiments, the one or more ligands of the one or more lipid-ligand conjugates are one or more therapeutic or diagnostic agent. Methods of production of a nanoparticle of the invention comprising a surface exposed lipid-ligand conjugate include the steps of (a) providing a nanoparticle and (b) associating the one or more lipid-ligand conjugates to the nanoparticle through adsorption or attachment to form a lipid-ligand coated nanoparticle. Alternatively the methods include the steps of (a) providing a nanoparticle, (b) associating the one or more ether-lipids to the nanoparticle through adsorption or attachement to form a lipid-coated nanoparticle and (c) covalently linking the one or more bioactive ligands to the one or more ether-lipids associated with the surface of the nanoparticle to form a lipid-ligand coated nanoparticle. The (preformed) lipid-coated nanoparticles are part of an application filed concurrently, which is incorporated herein in its entirety.

Typical methods to fabricate nanoparticles of suitable size include vaporization methods (e.g., free jet expansion, laser vaporization, spark erosion, electro explosion and chemical vapor deposition), physical methods involving mechanical attrition (e.g., the pearlmilling technology, Elan Nanosystems, Ireland), and interfacial deposition following solvent displacement.

In further embodiments, the invention is also directed towards a nanosphere comprising one or more lipid-ligand conjugates. As opposed to a nanoparticle, a nanosphere as a hollow interior, which may easily be used to enclose and subsequently deliver one or more bioactive agents to cells or tissues of interest. The release rate of such encapsulated bioactive agent(s) can be modulated, for example, by known techniques.

D. Pharmaceutical Compositions and Formulations

The carrier systems of the invention may be present as a pharmaceutical composition, e.g. which further comprises a pharmaceutically acceptable diluents, excipient or carrier, such as physiological saline or phosphate buffer, selected in accordance with the route of administration and standard pharmaceutical practice.

Thus in a further aspect the present invention is directed towards a pharmaceutical composition comprising one or more lipidic or nanoparticulate carrier system comprising ligand-lipid conjugates optionally in combination with other co-lipids and pharmaceutically acceptable diluents, excipient or carrier.

Preferably the lipidic carrier system is lipid vesicle, such as a liposome or a micelle and the nanoparticulate carrier system is a nanoparticle or nanosphere.

It is understood that the term "one or more lipid-ligand conjugates" refers to all possible embodiments as disclosed herein, i.e. conjugates wherein the ligand is one or more of a targeted, antigenic, therapeutic and diagnostic ligand and mixtures thereof. Optionally a further one or more bioactive agent is enclosed or embedded within or adsorbed onto or attached to the lipidic or nanoparticulate carrier system.

The pharmaceutical compositions of the present invention can be used in either in vitro, such as cell culture applications, or in vivo applications. With respect to in vivo applications, the lipid formulations of the present invention can be administered to a patient in a variety of forms adapted to the chosen route of administration, including parenteral, oral, or intraperitoneal administration. Parenteral administration includes intravenous, intramuscular, interstitially, intraarterially, subcutaneous, intraocular, intrasynovial, transepithelial (including transdermal), pulmonary via inhalation, ophthalmic, sublingual and buccal, topically (including ophthalmic, dermal, ocular, rectal), and nasal inhalation via insufflation administration, preferably intravenous administration.

The useful dosage to be administered and the particular mode of administration will vary depending upon the therapeutic or diagnostic use contemplated, the particular bioactive agent and lipid compound used as well as the form of the carrier system, e.g. micelle, liposome or nanoparticle, as well as factors such as age, weight, physical condition of the subject to be treated, as will be readily apparent to those skilled in the art. The use of targeted pharmaceutical compositions according to the invention allows administration of lower dosages for the desirable therapeutic effect to be achieved.

By way of general guidance, the ratio of lipid-ligand conjugate in the carrier system will vary from between 0.05 to 5 mole %, with a ratio of 0.1 to 2 mole % being more preferred, and between about 0.01 mg and about 10 mg of the particular antigenic, therapeutic or diagnostic agent each per kilogram of patient body weight, may be suitable to be administered, although higher and lower amounts can be used.

E. Methods of Use

As indicated above, in one specific embodiment the targeted lipid-ligand conjugates and in particular the targeted vesicles (i.e. liposomes and micelles) and targeted nanoparticles comprising these, as well as the respective pharmaceutical compositions thereof, are particularly suitable for use as carriers for a targeted delivery of one or more bioactive agents, preferably therapeutic, diagnostic and/or antigenic agents.

Thus, the targeted lipid-ligand conjugates of the present invention are particularly applicable for use in vitro and/or in vivo in methods for the treatment of diseases, for which a targeted delivery of one or more specific bioactive agents, preferably therapeutic, diagnostic and/or antigenic agents, to tissues or cells is desirable or required. In the case of targeted nanoparticles and pharmaceutical compositions thereof, the one or more bioactive agent is preferably entrapped within the solid core.

In the case of targeted lipid vesicles and pharmaceutical compositions thereof, the one or more bioactive agent is preferably enclosed within the internal void, or incorporated into the lipid bilayer.

In further aspects, the present invention also encompasses methods for transport of a diagnostic or biologically active compound across a membrane, in particular methods for intracellular delivery of one or more bioactive agent which comprises contacting cells with a pharmaceutical composition of the invention.

In another specific embodiment the antigenic vesicles (i.e. liposomes and micelles) and antigenic nanoparticles comprising these, as well as the respective pharmaceutical compositions thereof, are particularly suitable for use as antigen display systems. Thus, the antigenic lipid-ligand conjugates of the present invention are particularly applicable e.g. for use in immunization methods and/or for in vitro/in vivo diagnostic applications. Optionally the antigenic vesicles (i.e. liposomes and micelles) and antigenic nanoparticles may further comprise one or more bioactive agents. In case of antigenic nanoparticles, the one or more bioactive agent is preferably entrapped within the solid core. In the case of targeted lipid vesicles and pharmaceutical compositions thereof, the one or more bioactive agent is preferably enclosed within the internal void, or incorporated into the lipid bilayer.

Thus, in yet another aspect the present invention is directed towards an antigen display system for prophylactic and therapeutic vaccines which comprises an antigenic lipid vesicle or an antigenic nanoparticle comprising one or more antigenic lipid-ligand conjugates optionally in combination with other co-lipids, wherein the optionally comprises one or more adjuvants and/or one or more bioactive agents.

Also encompassed by the present invention are methods for triggering or modulating an immune response to an antigen in a subject which comprises the display of antigens to antigen presenting cells, in particular to dendritic cells, macrophages, B-cells and endothelial cells, and administering subsequently said antigen presenting cells to the subject. Other aspects of the invention include methods for transport of a biologically active compound across a membrane and/or methods of delivery of a biologically active compound into a cell using carrier systems of the invention.

Further applications that are contemplated include e.g. in vitro application for growth promotion and differentiation of cells as well as modification of expression profiles and post-translational modification patterns of biological products manufactured in bioreactors.

F. Kits

In yet a further aspect, the present invention relates to a kit comprised of a container that is compartmentalized for holding the various elements of the kit. One compartment may contain a predetermined quantity of either lipid-ligand conjugate or a carrier systems prepared therefrom In case of carrier systems such as liposomes, these may be with or without a pH buffer to adjust the composition pH to physiological range of about 7 to about 8, or else in lyophilized or freeze dried form for reconstitution at the time of use. Also included within the kit will be other reagents and instructions for use.

The present invention is further described in the following examples.

EXAMPLES

Materials:

1,2-Dioleoyl-sn-glycero-3-phosphocholine (DOPC) is from Merck & Cie (Schaffhausen, Switzerland). Cholesterol, DOPE, DSPC, POPC, MPEG2000-DOPE (880130), and fluorescent lipids NBD-DOPE (1,2-dioleoyl-sn-glycero-3-phosphoethanolamine-N-(7-nitro-2-1,3-benzoxadiazol-4-yl) (ammonium salt)) (810145P) and PhB-DOPE (810150) are purchased from Avanti Polar Lipids (Alabaster, Ala.). Functionalized PEG propionic acid (PA) derivative Fmoc-NH-PEG$_{12}$-PA-COOH (851024) is obtained from Novabiochem, Fmoc-NH-PEG$_8$-PA-COOH (PEG1830), Fmoc-NH-PEG$_{36}$-PA-COOH (PEG4400) and MPEG(2 kDa)-amine (PEG1152) from IRIS Biotech GmbH. Diphenyldiazomethane resin (D-2230) is obtained from Bachem AG, H-Thr(tBu)-2-ClTrt resin (RRA-1251) from CBL Patras, H-Gly-2-ClTrt resin (856053) and Sieber resin (855008) from Novabiochem. All other chemicals and solvents are A.R. grade or above.

Aza-peptide Michael acceptor trans-Cbz-D-Ala-D-Ala-2-aza-Asn-acrylic acid (RR11a-OH) and its activated ester with N-hydroxysuccinimide (RR11a-NHS) are synthesized by WuXi AppTec Co. Ltd. (Ekici et al, 2004, J. Med. Chem. 47, 1889-1892; Reisfeld et al., Nanomedicine: Nanotechnology, Biology and Medicine 7, Issue 6, 2011, 665-673). 2,3-Bis(tetradecyloxy)propan-1-amine is synthesized according to Kokotos et al. Chemistry-A European Journal, 2000, vol. 6, #22, 4211-4217. In an analogous way bis(3-((Z)-octadec-9-enyloxy)propyl)amine is obtained from oleyl methanesulfonate and bis(3-hydroxypropyl)amine (see MaGee et al., J. Journal of Organic Chemistry, 2000, vol. 65, #24, 8367-8371).

Cell Culture:

M21 human melanoma cells, obtained from Cell Culture Strain Collection, Merck KGaA, Darmstadt, Germany are maintained at 37° C. with 5% $CO_2$ in DMEM with High Glucose culture medium (Life Technologies, Carlsbad, Calif.) supplemented with 10% fetal bovine serum. Cells are regularly passaged and plated in 6-well culture plates for 16 hours before experiment at $0.3 \times 10^6$ cells in 2 ml medium. The M21 cells are incubated with liposomes in Opti-MEM serum free culture medium for 1 hour at 37° C., and then harvested using Cell Dissociation Buffer (Life Technologies, Carlsbad, Calif.) after one time wash with Opti-MEM. Colocalization of NBD-DOPE is determined by Guava easyCyte 8HT (EMD Millipore Corp., Billerica, Mass.).

Statistical Analysis:

Statistical analyses are preformed with Student's t-test. Differences among means are considered to be statistically significant at a p value of <0.01.

Example 1: Synthesis of (2S)-2-(((9H-fluoren-9-yl)methoxy)carbonylamino)-glutamic acid-α-tert-butylester-γ-2,3-bis(tetradecyloxy)propyl-amide

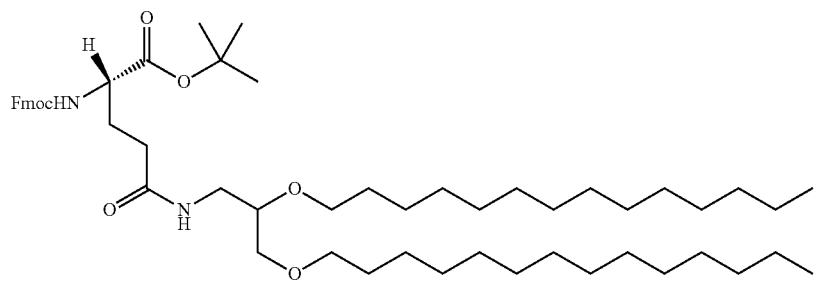

15 g of Fmoc-Glu(OSu)OtBu ((2S)—N$_{□}$-(9-fluorenylmethyloxycarbonyl)-glutamic acid α-tert-butyl-ester γ-N-hydroxysuccinimide ester) are dissolved in dichloromethane at room temperature. After addition of 15.3 g of 2,3-bis(tetradecyloxy)propan-1-amine, the mixture is stirred for 17 hours and evaporated to dryness. The residue is dissolved in a minimum amount of dichloromethane and purified by column chromatography using $SiO_2$ as solid phase and methyl tert. butylether/hexane/7:3 as eluent. After evaporation of product fractions 25.5 g of (2S)-2-(((9H-fluoren-9-yl)methoxy)carbonylamino)-glutamic acid-α-tert-butylester-γ-2,3-bis(tetradecyloxy)propyl-amide are obtained as a colorless solid. $^1$H-NMR in $CDCl_3$ (TMS as internal standard), chemical shift in ppm: 7.76 (d, 2H, Fmoc), 7.61 (d, 2H, Fmoc), 7.25-7.43 (m, 4H, Fmoc), 6.13 (bs, NH, 1H), 5.60 (bs, NH, 1H), 4.39, 4.18-4.25 (d and m, 4H), 3.21-3.62 (m, 9H), 1.97-2.23 (m, 4H), 1.51-1.60 (m, 4H), 1.47 (s, 9H), 1.25 (m, 44H, $CH_2$), 0.84-0.91 (m, 6H, 2× alkyl-$CH_3$).

Example 2: Synthesis of (2S)-2-(((9H-fluoren-9-yl)methoxy)carbonylamino)-glutamic acid-γ-2,3-bis(tetradecyloxy)propyl-amide

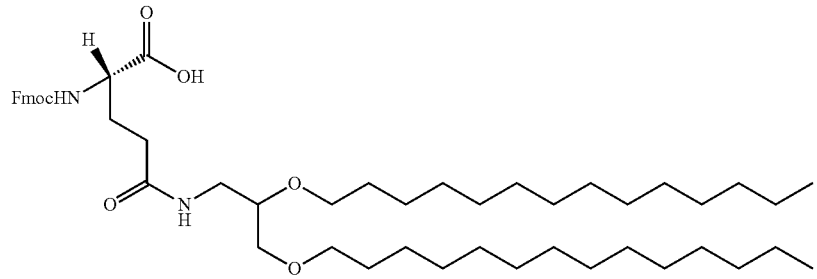

In a 100 ml flask 4.6 g (5.1 mmol) (2S)-2-(((9H-fluoren-9-yl)methoxy)carbonylamino)-glutamic acid-α-tert-butylester-γ-2,3-bis(tetradecyloxy)propyl-amide are dissolved in 25 ml dichloromethane and treated with 25 ml trifluoroacetic acid. After 1 h the ester group is completely cleaved and the solution is poured onto 50 ml of cold water.

The organic layer is extracted, washed to neutral pH with water and dried over $Na_2SO_4$. The organic layer is filtered off and the solvent evaporated to afford 4.2 g of the desired product (5.0 mmol, 98% yield, TLC: MtBE/hexane 7:3; Rf=0.43.

Example 3: Synthesis of (2S)-glutamic acid-γ-(2,3-bis(tetradecyloxy)propyl)amide

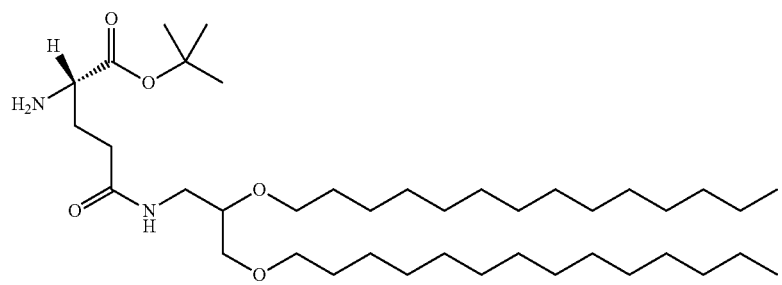 [SMILES: CCCCCCCCCCCCCCOCC(CNC(=O)CC[C@H](N)C(=O)OC(C)(C)C)OCCCCCCCCCCCCCC]

5 g of (2S)-2-(((9H-fluoren-9-yl)methoxy)carbonylamino)-glutamic acid-α-tert-butylester-γ-2,3-bis(tetradecyloxy)propyl-amide are added to 85 ml of N,N-dimethylformamide. To the mixture 2.6 ml of piperidine are added. The mixture is stirred for three hours at room temperature and then evaporated to dryness under vacuum to give 5.2 g of (2S)-glutamic acid-γ-(2,3-bis(tetradecyloxy)propyl)amide as a colorless solid, which can be used in the preparation of lipidic vesicles or for prior derivatization with an active agent or a spacer group.

Example 4: Synthesis of (R)-2-amino-N1-(2-(4-methoxybenzamido)ethyl)-N4,N4-bis(3-((Z)-octadec-9-enyloxy)propyl)succinamide (a) Synthesis of N-(2-aminoethyl)-4-methoxybenzamide

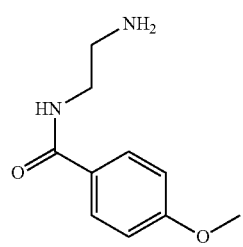

3.0 g 4-Methoxybenzoyl chloride are added to 30 mL 1,2-diaminoethane in dichloromethane at −78° C. and subsequently allowed to warm to 23° C. An aqueous acid-base workup and evaporation to dryness under vacuum give 1.65 g of N-(2-aminoethyl)-4-methoxybenzamide, a pale yellow oil. $^1$H-NMR in CDCl$_3$ (TMS as internal standard), chemical shift in ppm: 8.53 (t, 1H, NH), 7.91 (d, 2H, Benz), 6.99 (d, 2H, Benz), 4.75 (bs, 2H, NH$_2$), 3.81 (s, 3H, CH$_3$), 3.39, (dd, 2H, CH$_2$), 2.82 (t, 2H, CH$_2$).

(b) Synthesis of (R)-tert-butyl 3-(((9H-fluoren-9-yl)methoxy)carbonylamino)-4-(2-(4-methoxybenzamido)ethylamino)-4-oxobutanoate

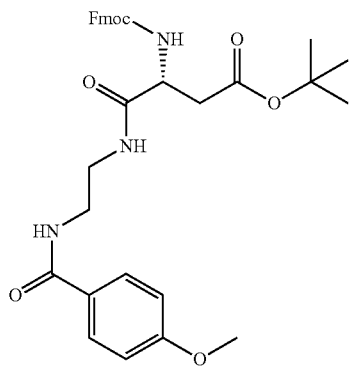

3.0 g 2 N-(2-aminoethyl)-4-methoxybenzamide (obtained in step (a)) and 1.70 mL N-methylmorpholine in DMF (0° C.) are added to a solution of 6.35 g Fmoc-Asp(OtBu)-OH, 1.70 mL N-methylmorpholine and 2.00 mL isobutylchloroformate in ethylacetate (−12° C.) and stirred for 3 h while allowing to warm to 23° C. Dilution of the resulting suspension with ethylacetate, followed by an aqueous acid-base workup and evaporation to dryness under vacuum yield 9.55 g (R)-tert-butyl 3-(((9H-fluoren-9-yl)methoxy)carbonylamino)-4-(2-(4-methoxybenzamido)ethylamino)-4-oxobutanoate. This crude material is suspended in isopropylether for 23 h, then filtered off and dried to furnish 4.47 g (R)-tert-butyl 3-(((9H-fluoren-9-yl)methoxy)carbonylamino)-4-(2-(4-methoxybenzamido)ethylamino)-4-oxobutanoate as white crystals. $^1$H-NMR in CDCl$_3$ (TMS as internal standard), chemical shift in ppm: 8.28 (t, 1H, NH), 8.07 (t, 1H, NH), 7.89 (d, 2H, Fmoc), 7.81 (d, 2H, Benz), 7.71-7.60 (m, 2H, Fmoc and 1H, NH), 7.46-7.27 (m, 4H, Fmoc), 6.96 (d, 2H, Benz), 4.35-4.20 (m, 3H, Fmoc, and 1H CH), 3.78 (s, 3H, CH$_3$), 3.40-3.20, (m, 4H, 2×CH$_2$), 2.69 (dd, 1H, CH$_2$), 2.46 (dd, 1H, CH$_2$), 1.37 (s, 9H, 3×CH$_3$).

(c) Synthesis of (R)-3-(((9H-fluoren-9-yl)methoxy)carbonylamino)-4-(2-(4-methoxybenzamido)ethylamino)-4-oxobutanoic sodium acetate

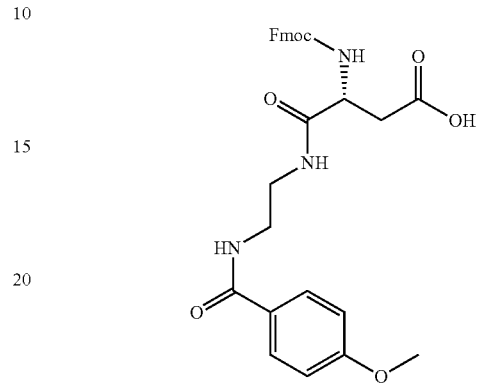

To 3.0 g (R)-tert-butyl 3-(((9H-fluoren-9-yl)methoxy)carbonylamino)-4-(2-(4-methoxybenzamido)ethylamino)-4-oxobutanoate (obtained in step (b)) in dichloromethane 30.0 mL trifluoroacetic acid are added at 23° C. Upon completion of the reaction aq. NaHCO$_3$ is added to furnish a white precipitate which is washed with dichloromethane and dried to yield 2.55 g (R)-3-(((9H-fluoren-9-yl)methoxy)carbonylamino)-4-(2-(4-methoxybenzamido)ethylamino)-4-oxobutanoic sodium acetate as a white powder. $^1$H-NMR in SO(CD$_3$)/CD$_3$OD, 1:1, (TMS as internal standard), chemical shift in ppm: 7.85-7.79 (m, 2H, Fmoc and 2H, Benz), 7.68 (d, 2H, Fmoc), 7.45-7.29 (m, 4H, Fmoc), 6.93 (d, 2H, Benz), 4.51-4.17 (m, 3H, Fmoc and 1H, CH), 3.78 (s, 3H, CH$_3$), 3.47-3.34, (m, 4H, 2×CH$_2$), 2.82 (dd, 1H, CH$_2$), 2.63 (dd, 1H, CH$_2$).

(d) Synthesis of (9H-fluoren-9-yl)methyl (R,Z)-1-(4-methoxyphenyl)-10-(3-((4-octadec-9-enyloxy)propyl)-1,6,9-trioxo-14-oxa-2,5,10-triazadotriacont-23-en-7-yl carbamate

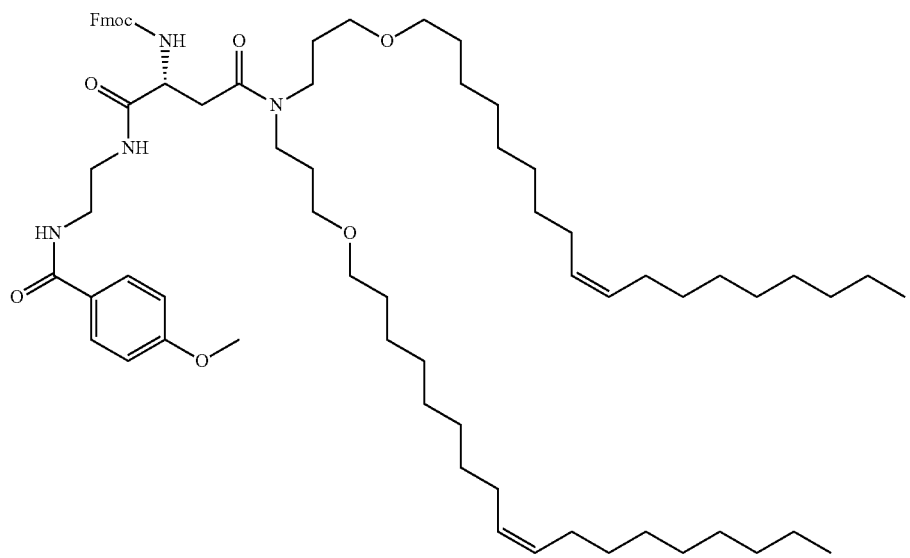

0.48 g (R)-3-(((9H-fluoren-9-yl)methoxy)carbonylamino)-4-(2-(4-methoxybenzamido)ethylamino)-4-oxobutanoic sodium acetate (obtained in step (c)) in dimethylformamide are cooled to 10° C. and then 0.46 g bis(3-((Z)-octadec-9-enyloxy)propyl)amine, 0.37 g COMU and 0.20 g DIPEA are added subsequently. After stirring at 23° C. for 20 h the solution is filtered through a pad of Alox and this rinsed with little dimethylformamide. The filtrate is diluted with ethylacetate, washed with water and evaporation to dryness under vacuum give 1.12 g orange oil which was purified by column chromatography to yield 0.41 g (9H-fluoren-9-yl)methyl (R,Z)-1-(4-methoxyphenyl)-10-(3-((Z)-octadec-9-enyloxy)propyl)-1,6,9-trioxo-14-oxa-2,5,10-triazadotriacont-23-en-7-yl-carbamate. $^1$H-NMR in CDCl$_3$ (TMS as internal standard), chemical shift in ppm: 7.86 (d, 2H, Benz), 7.69 (d, 2H, Fmoc), 7.55 (d, 2H, Fmoc), 7.42-7.23 (m, 4H, Fmoc and 1H, NH), 6.88 (d, 2H, Benz and 1H, NH), 6.12 (bd, 1H, NH), 5.41-5.26 (m, 4H, 4×CH), 4.60-4.33 (m, 3H, Fmoc), 4.17 (t, 1H, CH), 3.82 (s, 3H, CH$_3$), 3.62-3.23, (m, 16H, 8×CH$_2$ and 1H, CH$_2$), 2.73 (dd, 1H, CH$_2$), 2.05-1.95 (m, 8H, 4×CH$_2$), 1.85-1.65 (m, 4H, 2×CH$_2$), 1.57-1.45 (m, 4H, 2×CH$_2$), 1.24 (bs, 44H, 22×CH$_2$), 0.88 (t, 6H, 2×CH$_3$).

(e) Synthesis of (R)-2-amino-N1-(2-(4-methoxybenzamido)ethyl)-N4,N4-bis(3-((Z)-octadec-9-enyloxy)propyl)succinamide

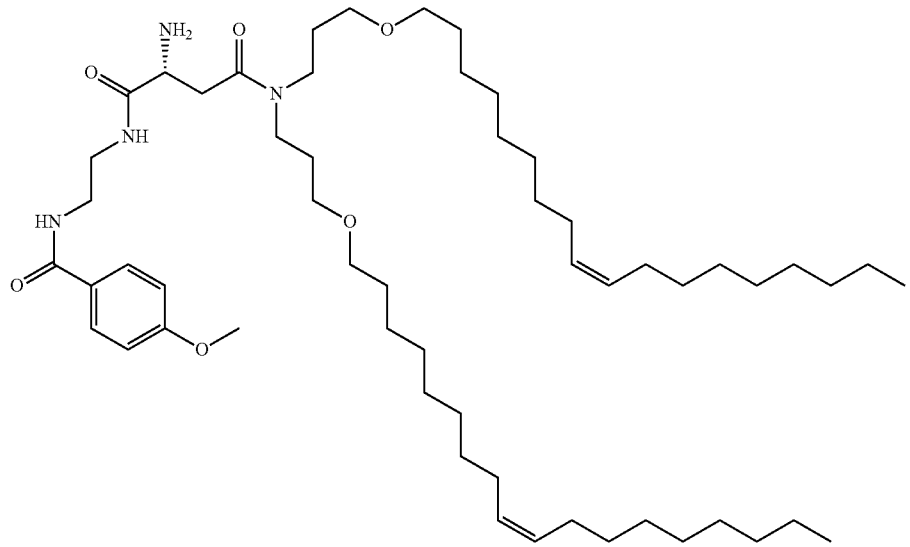 [SMILES: CCCCCCCC/C=C\CCCCCCCCOCCCN(CCCOCCCCCCCC/C=C\CCCCCCCC)C(=O)C[C@@H](N)C(=O)NCCNC(=O)c1ccc(OC)cc1]

To 2.12 g (9H-fluoren-9-yl)methyl (R,Z)-1-(4-methoxyphenyl)-10-(3-((Z)-octadec-9-enyloxy)propyl)-1,6,9-trioxo-14-oxa-2,5,10-triazadotriacont-23-en-7-yl-carbamate (obtained in step (d)) in dichloroethane 0.75 g diethylamine is added, stirred for 26 h followed by evaporation to dryness under vacuum to give 1.90 g crude material which is purified by adsorption to 20 g Dowex Monosphere and subsequent desorption by ammonia in ethanol to yield 1.09 g (R)-2-amino-N1-(2-(4-methoxybenzamido)ethyl)-N4,N4-bis(3-((Z)-octadec-9-enyloxy)propyl)succinamide. $^1$H-NMR in CDCl$_3$ (TMS as internal standard), chemical shift in ppm: 7.88 (d, 2H, Benz and 1H, NH), 7.64 (t, 1H, NH), 6.89 (d, 2H, Benz), 5.42-5.26 (m, 4H, 4×CH), 3.82 (s, 3H, CH$_3$), 3.65-3.49, (m, 4H, 2×CH$_2$), 3.42-3.28 (m, 12H, 6×CH$_2$ and 1H, CH), 2.99 (dd, 1H, CH$_2$), 2.71 (dd, 1H, CH$_2$), 2.10-1.92 (m, 8H, 4×CH$_2$ and 2H, NH$_2$), 1.85-1.67 (m, 4H, 2×CH$_2$), 1.60-1.47 (m, 4H, 2×CH$_2$), 1.28 (bs, 44H, 22×CH$_2$), 0.90 (t, 6H, 2×CH$_3$). MS: 947.9 [M+Na]$^+$.

Example 5: Synthesis of N$^2$,N,N-dimethylaminomethylene-10-formyl-folic acid-α-tert. butyl ester-vγ2,3 bis(tetradecyloxy) propylamide

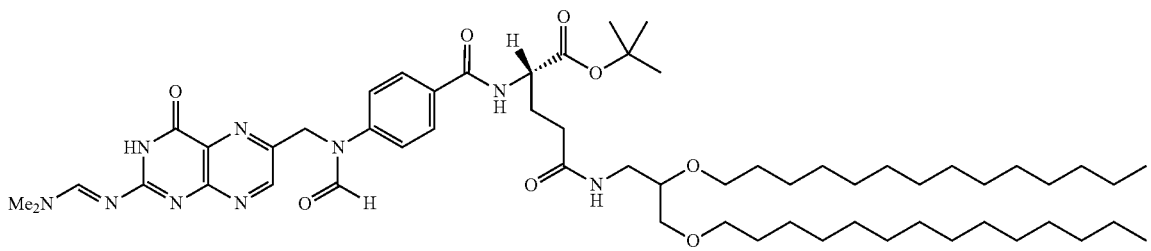 [SMILES: CCCCCCCCCCCCCCOCC(CNC(=O)CC[C@H](NC(=O)c1ccc(N(C=O)Cc2cnc3nc(/N=C/N(C)C)[nH]c(=O)c3n2)cc1)C(=O)OC(C)(C)C)OCCCCCCCCCCCCCC]

2.2 g of $N^2$,N,N-dimethylaminomethylene-10-formyl-pteroic acid are added to 46 ml of N,N-dimethylformamide. After addition of 3.2 g of 0-Benzotriazole-N,N,N',N'-tetramethyl-uronium-hexafluoro-phosphate the mixture is stirred for 20 minutes at room temperature. Then a mixture of 5.0 g of (2S)-glutamic acid-γ-(2,3-bis (tetradecyloxy)propyl) amide and 50 ml N,N-dimethylformamide is added dropwise. After stirring at room temperature for 17 hours, the solids are removed by filtration and the filtrate is evaporated to dryness in vacuum at 40° C. The residue is dissolved in 100 ml of dichloromethane. The dichloromethane solution is washed with 25 ml of aqueous citric acid solution, 25 ml of aqueous 5% sodium hydrogen carbonate solution and 25 ml of water. Each of the aqueous phases is extracted with dichloromethane. The combined dichloromethane phases are dried over magnesium sulphate, evaporated to dryness to give a yellow foam which is dissolved in a mixture of dichloromethane/methanol/95:5 and stirred for 15 min. at 40° C. Solids are removed by filtration and the filtrate is purified by column chromatography using $SiO_2$ as solid phase and dichloromethane/methanol/95:5 as eluent. After evaporation of product fractions 2.7 g of a yellow foam are obtained which are again purified by column chromatography as described above to give 2.2 g of $N^2$,N,N-dimethylaminomethylene-10-formyl-folic acid-α-tert. butyl ester-α-(2,3 bis(tetradecyloxy)propyl) amide as a pale yellow foam. $^1$H-NMR in $CDCl_3$ (TMS as internal standard), chemical shift in ppm: 10.00 (bs, 1H, N3-H), 8.96 (s, 1H, C7-H), 8.76, 8.72 (2s, 2H, CHN, CHO), 7.88 (d, 2H, C2'-H, C6'-H), 7.73 (d, 1H, NH(Glu)), 7.35 (d, 2H, C3'-H, C5'-H), 6.26 (d, 1H, C☐-NH), 5.32 (s, 2H, C6-$H_2$), 4.53 (m, 1H, CH-Glu), 3.30-3.56 (m, 9H, m, 4$CH_2$, CH—O-alkyl), 3.22 (s, 3H, N—$CH_3$), 3.15 (s, 3H, N—$CH_3$), 2.03-2.40 (m, 4H, 2 $CH_2$-Glu), 1.54 (m, s, 4H, 2$CH_2$), 1.46 (s, 9H, OC($CH_3$)$_3$), 1.24 (s, 44H, 22 $CH_2$), 0.87 (m, 6H, 2x alkyl-$CH_3$).

Example 6: Synthesis of folic acid-γ-(2,3 bis(tetradecyloxy)propyl)amide

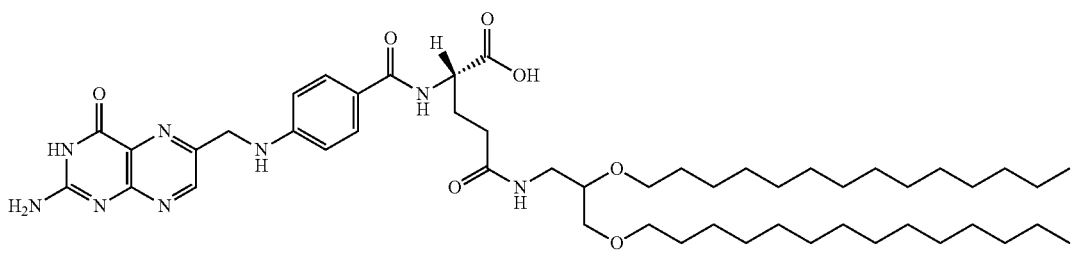 [SMILES: CCCCCCCCCCCCCCOCC(CNC(=O)CC[C@H](NC(=O)c1ccc(NCc2cnc3nc(N)[nH]c(=O)c3n2)cc1)C(=O)O)OCCCCCCCCCCCCCC]

2.1 g of $N^2$,N,N-dimethylaminomethylene-10-formyl-γ folic acid-α-tert. butyl ester-γ-2,3 bis(tetradecyloxy)propylamide are dissolved in 105 ml dichloromethane. After addition of 105 ml of trifluoroacetic acid the mixture is stirred for 1 hour at room temperature and then evaporated to dryness at 40° C. to give 3.4 g of a yellow foam. The latter is dissolved in 105 ml of tetrahydrofuran and 105 ml of 1M aqueous sodium hydroxide solution are added dropwise while stirring. The mixture is heated to 50° C. for 2.5 hours. After cooling to room temperature the organic layer is separated and evaporated to dryness. To the residue 105 ml of dichloromethane and 105 ml of 1 M aqueous hydrochloric acid are added. The mixture is stirred for 5 minutes at room temperature and the precipitated product is sucked off, washed with 500 ml of water and then dried at 40° C. in vacuum to 1.76 g of folic acid-γ-(2,3 bis(tetradecyloxy) propyl)amide as a yellow solid. $^1$H-NMR in DMSO-$d_6$ (TMS as internal standard), chemical shift in ppm: 11.59 (bs, 1H, N3-H), 8.64 (s, 1H, C7-H), 8.17 (d, 1H, NH), 7.81 (t, 1H, NH), 7.66 (d, 2H, C2'-H, C6'-H), 7.01 (bs, NH, 1H), 6.92 (t, 2H, NH), 6.64 (d, 2H, C3'-H, C5'-H), 4.49 (d, 2H, C6-$H_2$), 4.29 (m, 1H, CH-Glu), 3.26-3.46 (m, 5H, 2$CH_2$, CH—O-alkyl), 3.08 (s, 2H, $CH_2$), 2.17-2.2.5 (m, 2H, $CH_2$), 1.84-2.11 (2m, 2H, $CH_2$), 1.42, 1.23 (m, s, 44H, 22 $CH_2$), 0.85 (m, 6H, 2x alkyl-$CH_3$).

Example 7: Synthesis of (2S,47S)-47-[2-N-(dimethylamino)methylene]-10-formylpteroylamino-2-[3-[[2,3-bis(tetradecyloxy)propyl]amino]-3-oxopropyl]-4,44-dioxo-7,10,13,16,19,22,25,28,31,34,37,40-dodecaoxa-3,43-diazaoctatetracontane-1,48-dioic acid

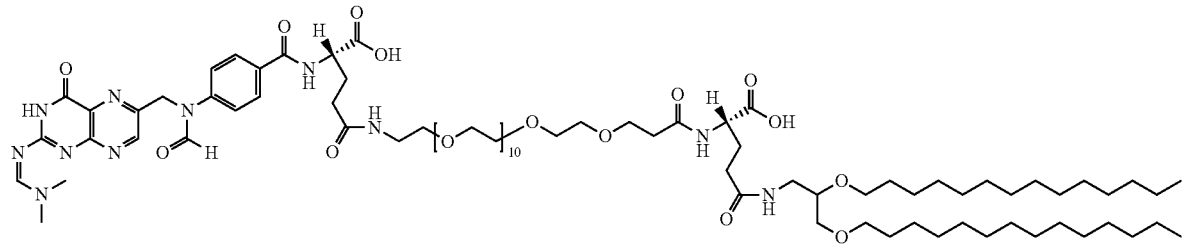

(a) Synthesis of Fmoc-Glu(DMA)-diphenylmethyl resin

In a 100 ml SPPS reactor 3.85 g of diphenyldiazomethane resin (3.3 mmol) are washed twice with 30 ml DCM and treated with a solution of 4.2 g of 2S)-2-(((9H-fluoren-9-yl)methoxy)carbonylamino)-glutamic acid-γ-2,3-bis(tetradecyloxy)propyl-amide (see example 2, 1.5 eq., 5.0 mmol) in 30 ml DCM over night. The solution is filtered off and the resin is washed with DCM four times. To destroy eventually un-reacted diphenyldiazomethane the resin is treated with 125 µl acetic acid (0.5 eq., 2.2 mmol) in 30 ml DCM for 15 minutes and washed afterwards three times alternating with 30 ml dimethylformamide and isopropanol. The resin is washed twice with diisopropyl ether and dried over night in vacuo. 6.7 g of the desired product are obtained (>100% of theory, yield in theory 6.5 g). The loading of the resin is determined to 0.49 mmol/g by UV measurement of the Fmoc cleavage product at 304 nm (maximum loading in theory 0.51 mmol/g).

(b) Synthesis of H-Glu-OtBu-NH-PEG$_{12}$-PA-Glu(DMA)-diphenylmethyl resin

H-Glu-OtBu-NH-PEG$_{12}$-PA-Glu(DMA)-diphenylmethyl resin is obtained through conventional solid phase synthesis by the following reaction sequence:
(1) cleavage of the Fmoc group of the Fmoc-Glu(DMA)-diphenylmethyl resin with piperidin in DMF,
(2) condensation with Fmoc-NH-PEG$_{12}$-PA-COOH using HBTU in DMF and DIPEA,
(3) cleavage of the Fmoc group of the Fmoc-NH-PEG$_{12}$-PA-Glu(DMA)-diphenylmethyl resin with piperidin in DMF,
(4) condensation with Fmoc-Glu-OtBu using HBTU in DMF and DIPEA and finally
(5) cleavage of the Fmoc group of the Fmoc-Glu-OtBu-NH-PEG$_{12}$-PA-Glu(DMA)-diphenylmethyl resin with piperidin in DMF.

(c) Synthesis of [2-N-(dimethylamino)methylene]-10-formylpteroyl-Glu-OtBu-NH-PEG$_{12}$-PA-Glu(DMA)-diphenylmethyl resin

[2-N-(dimethylamino)methylene]-10-formylpteroyl-Glu-OtBu-NH-PEG$_{12}$-PA-Glu(DMA)-diphenylmethyl resin is obtained through conventional solid phase synthesis by reacting H-Glu-OtBu-NH-PEG$_{12}$-PA-Glu(DMA)-diphenylmethyl resin in DMF with [2-N-(dimethylamino)methylene]-10-formylpteroic acid, HATU and DIPEA.

(d) Synthesis of (2S,47S)-47-[2-N-(dimethylamino)methylene]-10-formylpteroylamino-2-[3-[[2,3-bis(tetradecyloxy)propyl]amino]-3-oxopropyl]-4,44-dioxo-7,10,13,16,19,22,25,28,31,34,37,40-dodecaoxa-3,43-diazaoctatetracontane-1,48-dioic acid 4.5 g [2-N-(dimethylamino)methylene]-10-formylpteroyl-Glu-OtBu-NH-PEG$_{12}$-PA-Glu(DMA)-diphenylmethyl resin are washed with 45 ml dichloromethane, filtered off and suspended again in 45 ml dichloromethane. Then 41.4 ml of trifluaroacetic acid are added followed by 2.25 ml triisopropylsilane. The suspension is stirred at room temperature for 1 hour and then filtered. The resin is washed three times with 45 ml dichloromethane each. The combined filtrates are evaporated in vacuo to yield 5.75 g of an amber oil. HPLC: 90.7% area, ESI-MS: monoisotopic $M_{W\ calc.}$=1718.1, $M_W$ [M−H]$^−$=1718.0.

Example 8: Synthesis of (2S,47S)-47-pteroylamino-2-[3-[[2,3-bis(tetradecyloxy)propyl]amino]-3-oxopropyl]-4,44-dioxo-7,10,13,16,19,22,25,28,31,34,37,40-dodecaoxa-3,43-diazaoctatetracontane-1,48-dioic acid

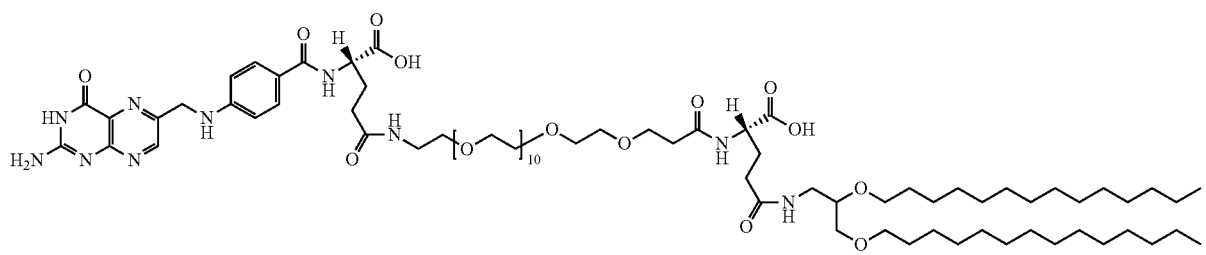

4.6 g (2S,47S)-47-[2-N-(dimethylamino)methylene]-10-formylpteroylamino-2-[3-[[2,3-bis(tetradecyloxy)propyl]amino]-3-oxopropyl]-4,44-dioxo-7,10,13,16,19,22,25,28,31,34,37,40-dodecaoxa-3,43-diazaoctatetracontane-1,48-dioic acid are stirred with 460 ml 1N NaOH at 50° C. for 2 hours. The reaction mixture is brought to pH 12.5 by the addition of 59.2 g 32% ic NaOH. The brown solution is treated with 0.46 g activated carbon for 15 min at 50° C., filtered hot and brought to pH 1 by the addition of 3.2 g 37% ic HCl. The resulting precipitate is collected by filtration, washed with water and dried at room temperature in vacuo to yield 1.2 g of a greenyellow solid. H PLC: 89.9% area, ESI-MS: monoisotopic $M_{W\ calc.}$=1635.0, $M_W$ [M−H]$^−$=1634.1.

Example 9: Synthesis of RGD Lipid Pentapeptide Cyclo[-Asp-hGlu(DMA)-D-Val-Arg-Gly-]

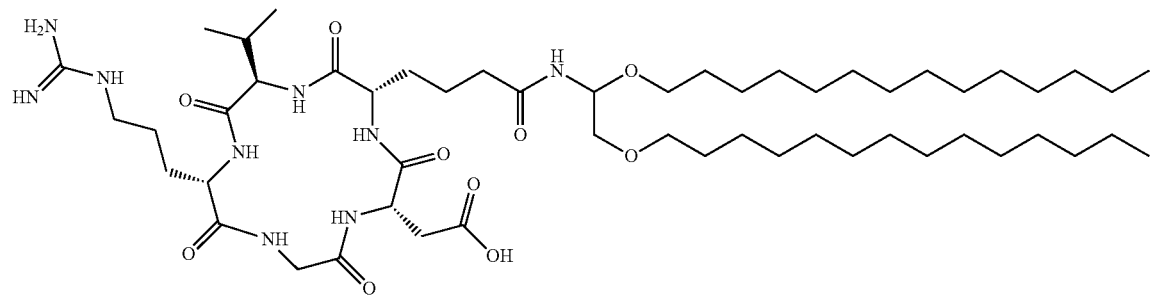 [SMILES: CCCCCCCCCCCCCCOCC(NC(=O)CCC[C@@H]1NC(=O)[C@H](CC(=O)O)NC(=O)CNC(=O)[C@H](CCCNC(=N)N)NC(=O)[C@@H](C(C)C)NC1=O)OCCCCCCCCCCCCCC]

(a) Synthesis of Fmoc-hGlu(OBzl)-OH

Commercially available homo glutamic acid (H-hGlu-OH) is side chain protected as δ-benzyl ester following a published protocol (Benoiton L., *Can. J. Chem.*, 40, 570 (1962)) (yield: 19.8 g, 26% of theory, TLC (CHCl$_3$/MeOH/32% acetic acid 5:3:1) $R_f$=0.62). Without further purification H-hGlu(OBzl)-OH (19.7 g, 77.6 mmole) is dissolved in a mixture of dioxane/water (1:2, 300 ml) and Fmoc protected by addition of NaHCO$_3$ (12.8 g, 155 mmole) and Fmoc-OSu (26.2 g, 77.6 mmole). After completion the reaction mixture is extracted three times with diisopropylether. The product containing aqueous layer is adjusted to pH 2 with HCl and the product is extracted with ethyl acetate three times. The combined organic layers are washed with H$_2$O to neutral pH. The ethyl acetate is evaporated and the residual water removed as an azeotrope with acetonitrile. Therefore the product is obtained as a dry foam: 34.9 g, 73.7 mmole, 95% of the theory, ESI-MS: monoisotopic $M_{W\ calc.}$=473.2, $M_W$ [M+H]$^+$=474.1.

(b) Synthesis of H-Asp(OtBu)-hGlu(OBzl)-D-Val-Arg(Pbf)-Gly-OH

The solid phase peptide synthesis is carried out following the Fmoc/tBu strategy (Atherton E., et. al., *J. Chem. Soc., Chem. Comm.*, 539 (1978)), H-Gly-2-ClTrt (46 g, 34.5 mmole) is used as the base resin, coupling is performed by Fmoc-Xaa-OH/DIC/HOBt (2 eq.:4 eq.:3 eq.) over night, the removal of the Fmoc protection is achieved by 20% piperidine in DMF after 5 and 10 min. Alternating washing steps three times with dimethylformamide/isopropanol are employed after each coupling and de-protection step respectively. The amino acid derivatives used in their chronological order are Fmoc-Arg(Pbf)-OH, Fmoc-D-Val-OH, Fmoc-homoGlu(OBzl)-OH and Fmoc-Asp(OtBu)-OH. The Fmoc-SPPS yields 73.4 g of linear peptide resin (weight gain of the resin 27.4 g, 87% of the theory, theory=31.5 g).

The side chain protected linear pentapeptide is cleaved from the resin (72.0 g) by a mixture of 1,1,1,3,3,3-hexafluoro-2-propanol/dichloromethane 1:4 (700 ml) in three repetitions. The solvents of the combined filtrates are removed under reduced pressure and the resulting oil stirred in cold methyl-t-butylether (1 L) to yield an off-white precipitate which is filtered off, washed three times with methylt-butylether and dried in vacuo: 23.6 g, 23.9 mmole, 70% of theory with regard to the loading of the base resin, >40 area % on HPLC, retention time of 14.1 min (HPLC conditions: column=Halo® Peptide ES-C18, 4.6×150 mm, 2.7 µm, gradient: linear acetonitrile gradient from 25% to 90% B in 30 min., buffer A=0.1% TFA and 2% acetonitrile in water, buffer B=0.1% TFA in acetonitrile, wavelength=210 nm), ESI-MS: monoisotopic $M_{W\ calc.}$=986.5, $M_W$ [M+H]$^+$=987.6.

(c) Synthesis of Cyclo[-Asp(OtBu)-hGlu(OBzl)-D-Val-Arg(Pbf)-Gly-]

The linear side chain protected pentapeptide H-Asp(OtBu)-hGlu(OBzl)-D-Val-Arg(Pbf)-Gly-OH (23.6 g, 23.9 mmole) and the in-situ activation reagent PyBOP (12.4 g, 23.9 mmol) are dissolved in 10 L of dimethylformamide (DMF) and added drop wise within 3 h to a solution of additional PyBOP (24.9 g, 47.8 mmole) and Hünig's base (16.4 ml, 95.6 mmole) in 5 L DMF. The resulting solution is stirred over night. The DMF is removed in vacuo and the obtained oil dissolved under reflux in 1.8 L ethanol and crystallized by the addition of 3.2 L of water at −18° C. The precipitate is filtered off and washed with water and ether. In addition it is further purified by silica gel chromatography (150 g silica gel 60, eluent: dichloromethane/methanol 9:1) resulting in 3.6 g of the cyclic pentapeptide with a purity >91 area % on HPLC (HPLC conditions: column=Halo® Peptide ES-C18, 4.6×150 mm, 2.7 µm, gradient: linear acetonitrile gradient from 25% to 90% B in 30 min., buffer A=0.1% TFA and 2% acetonitrile in water, buffer B=0.1% TFA in acetonitrile, wavelength=210 nm); 3.7 mmole, 15% of theory, retention time 15.8 min, ESI-MS: monoisotopic $M_{W\ calc.}$=968.4, $M_W$ [M+H]$^+$=969.5.

(d) Synthesis of Cyclo[-Asp(OtBu)-hGlu-D-Val-Arg(Pbf)-Gly-]

The benzyl ester is specifically cleaved by hydrogenolysis. For this, 3.6 g (3.7 mmole) of cyclo[-Asp(OtBu)-hGlu (OBzl)-D-Val-Arg(Pbf)-Gly-] are dissolved in 20 ml DMF and diluted with 2 L methanol. After addition of 5 g of 5% palladium on activated charcoal to this solution, the mixture is hydrogenated. Upon completion the catalyst is filtered off and the solution concentrated under reduced pressure. The product is precipitated in methyl-t-butylether to yield 3.0 g of the desired product: 3.4 mmole, yield 93% of the theory, purity: 75 area % on HPLC (HPLC conditions: column=Halo® Peptide ES-C18, 4.6×150 mm, 2.7 µm, gradient: linear acetonitrile gradient from 25% to 90% B in 30 min., buffer A=0.1% TFA and 2% acetonitrile in water, buffer B=0.1% TFA in acetonitrile, wavelength=210 nm), retention time 13.8 min.

(e) Synthesis of Cyclo[-Asp-hGlu(DMA)-D-Val-Arg-Gly-]

1.5 g (1.7 mmole) of the cyclo pentapeptide cyclo[-Asp(OtBu)-hGlu-D-Val-Arg(Pbf)-Gly-] are conjugated to 2,3-dimyristyl-1-amino-sn-glycerol (DMA; 1.0 g, 2.0 mmole) in 100 ml DMF by PyBOP/DIPEA activation (0.9 g, 1.7 mmol/0.6 ml, 3.4 mmole). The reaction mixture is stirred over night. Then 200 ml dichloromethane are added and the organic phase is extracted three times with 50 ml 2% KHSO$_4$ and three times with water. The organic layer is evaporated under reduced pressure and the residual water removed as an azeotrope with acetonitrile. The resulting foam is directly treated with the final cleavage cocktail TFA/H$_2$O/tri-isopropylsilane/dithioerythritol (92.5:2.5:2.5:2.5) for 1.5 hours and afterwards the solution added drop wise to cold diisopropylether (5° C.) in order to precipitate the desired product. The residue is then separated by filtration, washed twice with diisopropylether and in addition dried in vacuo to give 0.5 g of the title compound: 0.5 mmole, 30% of the theory, >93.0 area % on HPLC (HPLC conditions: column=Zorbax SB-C3, 4.6×250 mm, 5 µm, gradient: linear acetonitrile gradient from 30% to 100% B in 25 min., buffer A=0.1% TFA and 2% acetonitrile in water, buffer B=0.1% TFA in acetonitrile, wavelength=210 nm), retention time of 22.0 min, ESI-MS: monoisotopic $M_{W\ calc.}$=1035.8, $M_W$ [M+H]$^+$=1037.1.

Example 10: Preparation of pVision-RFP-C Vector Containing, Folate Decorated Liposomes 478.2 mg POPC, 58.8 mg Chol, 13.5 mg folate-lipid (see example 8) and 2 µg 7-nitrobenzofurazan-labelled-DOPE are dissolved in 750 µL ethanol (96%) at 60° C. and injected into 4.25 mL of a RFP plasmide containing PBS pH 7.4 (1.27 mg RFP-Plasmid/mL). Molar ratio of the used lipids is 77.99:18.83:1.02:0.27. After extrusion through 200 nm polycarbonate membrane for 5 times and 100 nm polycarbonate membrane for 5 times and diafiltration the liposomes have an average size of 161 nm with a PDI of 0.13. The molar ratio of POPC:Chol is 77.99:15.76, Folate-lipid content is 502 µg/ml (targeted 770 µg/ml) according to HPLC analysis.

Example 11: Preparation of Anis Amide Decorated Liposomes 470 mg POPC, 60 mg Chol and 13.5 mg anis amide lipid (see example 4) are dissolved in 750 µL ethanol (96%) at 55° C. and injected into 4.25 mL of PBS pH 7.4. Molar ratio of the used lipids is 77.99:18.83:1.02:0.27. After extrusion through 100 nm polycarbonate membrane the liposomes have an average size of 110 nm with a PDI of 0.068. According to HPLC analysis the anis amide lipid content is 72% of the theoretical value.

Example 12: Preparation of RGD Decorated Liposomes

A mixture of DOPC, Chol, NBD-DOPE, and the RGD-lipid obtained in Example 9 in a molar ratio of DOPC:Chol:NBD-DOPE:RGD-lipid 66:33:0.5:0~5 are used to prepare liposomes by dry film method in HEPES buffer, followed by extrusion through 200 nm polycarbonate membrane for 5 times and 100 nm polycarbonate membrane for 21 times using Lipofast extruder (Avestin, Inc., Ottawa, Canada). The obtained liposomes are stored at 4° C. until use.

Example 13: Cellular Uptake of RGD Decorated Liposomes

The extent of cellular uptake for RGD decorated liposomes (obtained in Example 6) on M21 cells are evaluated on the basis of NBD-DOPE signal detected by Guava easyCyte 8HT flowcytometer and is illustrated in FIG. 1 and Table 1.

TABLE 1

| | NBD positive cells (%) | | | | | | Avg | SD |
|---|---|---|---|---|---|---|---|---|
| Blank | 0.19 | 0.36 | 0.4 | 0.33 | 0.29 | 0.65 | 0.37 | 0.15 |
| 0% RGD | 1.04 | 1.75 | 1.56 | 1.57 | 1.37 | 1.66 | 1.49 | 0.25 |
| 5% RGD | 29.99 | 28.41 | 23.77 | 24.82 | 23.68 | 20.99 | 25.28 | 3.33 |

About a 16 fold enhancement in cellular uptake is observed for the RGD targeting liposome (5% DMA-RGD) as compared to non-targeting liposome (0% DMA-RGD). The x-axis represents the molar ratio of DMA-RGD (%) in the liposome. The y-axis represents NBD-positive cells (%). FIG. 1 illustrates that the RGD moieties can recognize target receptors (Integrin $\alpha_v\beta_3$ receptors) expressed on M21 cells (* p<0.01).

Example 14: Synthesis of (5S,8S,45S,E)-11-(2-amino-2-oxoethyl)-45-(3-((2,3-bis(tetradecyloxy)propyl)amino)-3-oxopropyl)-5,8-dimethyl-3,6,9,12,15,43-hexaoxo-1-phenyl-2,19,22,25,28,31,34,37,40-nonaoxa-4,7,10,11,16,44-hexaazahexatetracont-13-en-46-oic acid

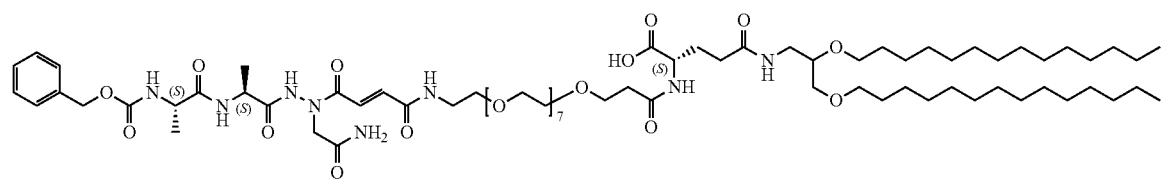

(a) Synthesis of Fmoc-Glu(DMA)-Diphenylmethyl Resin (See Example 7, 1.1 Eq., 3.05 Mmol)

(b) Synthesis of RR11a-NH-PEG$_8$-PA-Glu(DMA)-diphenylmethyl resin

RR11a-NH-PEG$_8$-PA-Glu(DMA)-diphenylmethyl resin is obtained through conventional solid phase synthesis by the following reaction sequence:
(1) cleavage of the Fmoc group of the Fmoc-Glu(DMA)-diphenylmethyl resin with piperidin in DMF,
(2) condensation with Fmoc-NH-PEG$_8$-PA using PyBOP in DMF and DIPEA,
(3) cleavage of the Fmoc group of the Fmoc-NH-PEG$_8$-PA-Glu(DMA)-diphenylmethyl resin with piperidin in DMF and finally
(4) condensation with RR11a-OH using PyBOP in DMF and DIPEA.

(c) Synthesis of (5S,8S,45S,E)-11-(2-amino-2-oxoethyl)-45-(3-((2,3-bis(tetradecyloxy)propyl)amino)-3-oxopropyl)-5,8-dimethyl-3,6,9,12,15,43-hexaoxo-1-phenyl-2,19,22,25,28,31,34,37,40-nonaoxa-4,7,10,11,16,44-hexaazahexatetracont-13-en-46-oic acid 7.15 g RR11a-NH-PEG$_8$-PA-Glu(DMA)-diphenylmethyl resin are washed with 50 ml dichloromethane each, filtered off, suspended again in 50 ml dichloromethane and dried in vacuo. Then 70 ml of a 5% ic solution of trifluaroacetic acid in dichloromethane were added. The suspension is stirred at room temperature for 3.5 hour and then filtered into 100 ml cold diisopropylether. The resin is rinsed with dichloromethane/diisopropylether (1/1). The combined filtrates are evaporated in vacuo and lyophilyzed from t-BuOH to yield 4.15 g (92%) of an amber solid. ESI-MS: monoisotopic $M_{W\ calc.}$=1481.9, $M_W$ [M−H]$^−$=1480.2.

Example 15: Synthesis of (5S,8S,45S,E)-11-(2-amino-2-oxoethyl)-45-(3-((2,3-bis(tetradecyloxy)propyl)amino)-3-oxopropyl)-5,8-dimethyl-3,6,9,12,15,43-hexaoxo-1-phenyl-2,19,22,25,28,31,34,37,40-nonaoxa-4,7,10,11,16,44-hexaazahexatetracont-13-en-46-oic acid

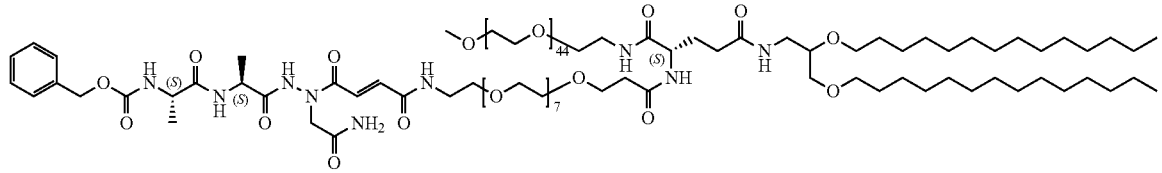

7.15 g RR11a-NH-PEG$_8$-PA-Glu(DMA)-OH (product of Example 14) and 1.50 ml DIPEA are dissolved in 70 ml dichloromethane. Then 4.32 g MeO-PEG-NH2 and 1.67 g PyBOP are added and the solution is stirred overnight. The brown solution is evaporated and the residue is purified twice by column chromatography over 300 g silica gel (Merck 60, 0.040-0.063 mm) using a mixture of ethylacetat, methanol and triethylamine in a ratio of 16:3.1 resp. 17:2:1. The product containing fractions are combined and evaporated and the resulting viscous residue is lyophilized from t-BuOH to yield 4.5 g (60%) of an yellowish solid. MALDI-MS: monoisotopic $M_{W\ calc.}$=3476.2, $M_W$ [M+Na]+=3500, $M_n$=3363.2, $M_W$=3384.5, PDI=1.01

Example 16: Synthesis of benzyl ((2S,5S,14S,E)-8-(2-amino-2-oxoethyl)-14-carbamoyl-5-methyl-3,6,9,12,17-pentaoxo-20-(tetradecyloxy)-22-oxa-4,7,8,13,18-pentaazahexatriacont-10-en-2-yl)carbamate

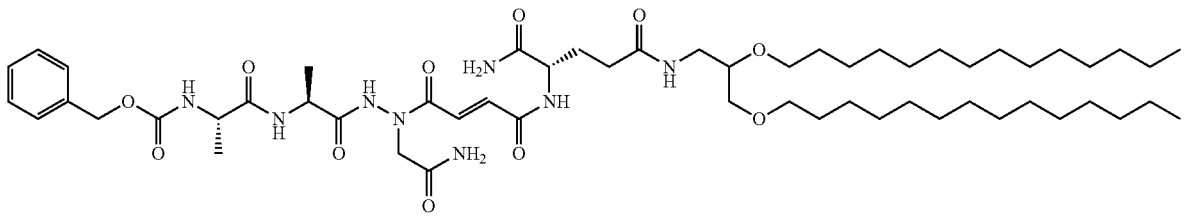 [SMILES: CCCCCCCCCCCCCCOCC(CNC(=O)CC[C@H](NC(=O)/C=C/C(=O)N(CC(N)=O)NC(=O)[C@H](C)NC(=O)[C@H](C)NC(=O)OCc1ccccc1)C(N)=O)OCCCCCCCCCCCCCC]

(a) Synthesis of Fmoc-Glu(DMA)-Sieber Resin

In a 100 ml SPPS reactor 5.0 g of Sieber resin (3.1 mmol) are washed twice with 50 ml DMF, treated with a 20% ic solution of piperidine in DMF over 15 min and washed three times alternatingly with 50 ml DMF and with 50 ml iPrOH. Then a solution of 3.2 g of (2S)-2-(((9H-fluoren-9-yl)methoxy)carbonylamino)-glutamic acid-γ-2,3-bis(tetradecyloxy)propyl-amide (see example 2, 1.25 eq., 3.8 mmol) and 2.48 g PyBOP (1.5 equ.) in 50 ml DMF, and 1.62 ml DIPEA (2.5 equ.) for 2.5 h. The solution is filtered off and the resin is washed three times alternatingly with 50 ml DMF and with 50 ml iPrOH.

(b) Synthesis of RR11a-Glu(DMA)-Sieber Resin

RR11a-Glu(DMA)-Sieber resin is obtained through conventional solid phase synthesis by the following reaction sequence:

(1) cleavage of the Fmoc group of the Fmoc-Glu(DMA)-Sieber resin with piperidin in DMF (5.6 g resin after drying in vacuo).

(2) condensation with RR11a-NHS using DIPEA in DMF.

(c) Cleavage of the Product from the Resin:

2.6 g RR11a-Glu(DMA)-Sieber resin are treated with 20 ml 5% ic trifluaroacetic acid in dichloromethane for 2 h. The suspension is filtered into 100 ml cold diisopropylether. The filtrate is evaporated in vacuo and lyophilyzed from t-BuOH to yield 660 mg of a yellowish solid. ESI-MS: monoisotopic $M_{W\ calc.}$=1056.7, $M_W$ [M−H]$^-$=1056.0.

Example 17: Synthesis of benzyl ((2S,5S,42S,E)-8-(2-amino-2-oxoethyl)-42-carbamoyl-5-methyl-3,6,9,12,40,45-hexaoxo-48-(tetradecyloxy)-16,19,22,25,28,31,34,37,50-nonaoxa-4,7,8,13,41,46-hexaazatetrahexacont-10-en-2-yl)carbamate

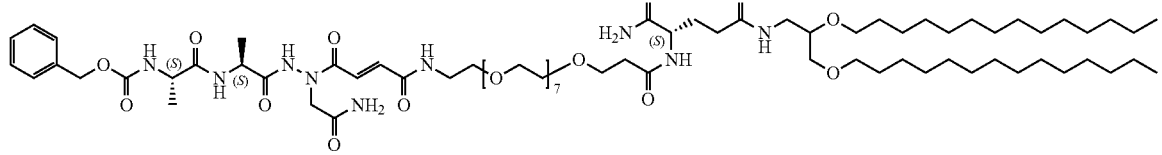

(a) Synthesis of Fmoc-Glu(DMA)-Sieber Resin:
(See Example 16)

(b) Synthesis of NH$_2$-PEG$_8$-PA-Glu(DMA)-Sieber Resin

NH$_2$-PEG$_8$-PA-Glu(DMA)-Sieber resin is obtained through conventional solid phase synthesis by the following reaction sequence:

(1) cleavage of the Fmoc group of the Fmoc-Glu(DMA)-Sieber resin with piperidin in DMF, (2) condensation with Fmoc-NH-PEG$_8$-PA using HBTU in DMF and DIPEA and finally (3) cleavage of the Fmoc group of the Fmoc-NH-PEG$_8$-PA-Glu(DMA)-Sieber resin with piperidin in DMF.

(c) Synthesis of NH$_2$-PEG$_8$-PA-Glu(DMA)-Amide

The product is cleaved from the NH$_2$-PEG$_8$-PA-Glu(DMA)-Sieber resin using trifluaroacetic acid in dichloromethane. ESI-MS: monoisotopic $M_{W\ calc.}$=1034.8, $M_W$ [M+H]$^+$=1035.9.

(d) Synthesis of benzyl ((2S,5S,42S,E)-8-(2-amino-2-oxoethyl)-42-carbamoyl-5-methyl-3,6,9,12,40,45-hexaoxo-48-(tetradecyloxy)-16,19,22,25,28,31,34,37,50-nonaoxa-4,7,8,13,41,46-hexaazatetrahexacont-10-en-2-yl)carbamate A 5 ml round bottom flask equipped with mechanical stirrer is charged with 42 mg of NH$_2$-PEG8-PA-Glu(DMA)-amide (40.6 mmol) in 2 ml dichloromethane. Then 0.01 ml triethylamine (95 mmol) are added. A light yellow solution results after 2-3 minutes of stirring and 23 mg of RR11a-NHS (41 mmol) are added over a period of 3 min. The solution is stirred for 1 hr and evaporated under reduced pressure resulting in a off-white solid product. The product shows a single spot in TLC. $M_{W\ calc.}$=1480.0, $M_W$ [M+H]$^+$=1482 and $M_W$ [M+Na]$^+$=1504.0.

Example 18: Synthesis of benzyl ((2S,5S,126S,E)-8-(2-amino-2-oxoethyl)-126-carbamoyl-5-methyl-3,6,9,12,124,129-hexaoxo-132-(tetradecyloxy)-16,19,22,25,28,31,34,37,40,43,46,49,52,55,58,61,64,67,70,73,76,79,82,85,88,91,94,97,100,103,106,109,112,115,118,121,134-heptatriacontaoxa-4,7,8,13,125,130-hexaazaoctatetracontahect-10-en-2-yl)carbamate

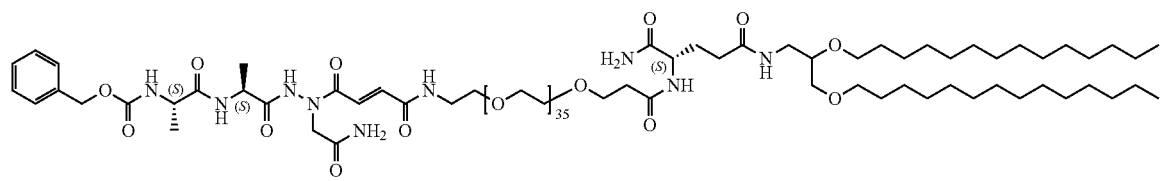

(a) Synthesis of Fmoc-Glu(DMA)-Sieber Resin: (See Example 16)

(b) Synthesis of RR11a-NH-PEG$_{36}$-PA-Glu(DMA)-Sieber Resin

RR11a-NH-PEG$_{36}$-PA-Glu(DMA)-Sieber resin is obtained through conventional solid phase synthesis by the following reaction sequence:

(1) cleavage of the Fmoc group of the Fmoc-Glu(DMA)-Sieber resin with piperidin in DMF,
(2) condensation with Fmoc-NH-PEG$_{36}$-PA using PyBOP in DMF and DIPEA,
(3) cleavage of the Fmoc group of the Fmoc-NH-PEG$_{36}$-PA-Glu(DMA)-Sieber resin with piperidin in DMF and finally
(4) condensation with RR11a-NHS using DIPEA in DMF.

(c) Synthesis of benzyl ((2S,5S,126S,E)-8-(2-amino-2-oxoethyl)-126-carbamoyl-5-methyl-3,6,9,12,124,129-hexaoxo-132-(tetradecyloxy)-16,19,22,25,28,31,34,37,40,43,46,49,52,55,58,61,64,67,70,73,76,79,82,85,88,91,94,97,100,103,106,109,112,115,118,121,134-heptatriacontaoxa-4,7,8,13,125,130-hexaazaoctatetracontahect-10-en-2-yl)carbamate 7.0 g RR11a-NH-PEG$_{36}$-PA-Glu(DMA)-Sieber resin are treated with 70 ml of a 2% ic solution of trifluaroacetic acid in dichloromethane are added. The suspension is stirred at room temperature for 3 h and then filtered into 70 ml cold diisopropylether. The filtrate is evaporated in vacuo and lyophilyzed from t-BuOH to yield 1.25 g of a white solid. ESI-MS: monoisotopic $M_W$ $_{calc.}$=2713.7, $M_W$ [M+Na+H]$^{2+}$=1380.1.

Example 19: Preparation of RR11a Decorated Liposomes

RR11a decorated liposomes (MS 15-4) and control liposomes (MS 15-0) are composed from the following lipid solutions:

| lipid | concentration in chloroform | volume MS 15-0 | volume MS 15-4 |
|---|---|---|---|
| DOPE | 33 mM | 35 µl | 35 µl |
| DSPC | 32 mM | 35 µl | 35 µl |
| Cholesterol | 33 mM | 35 µl | 35 µl |

-continued

| lipid | concentration in chloroform | volume MS 15-0 | volume MS 15-4 |
|---|---|---|---|
| MPEG2000-DOPE | 18 mM | 15 µl | 15 µl |
| RhB-DOPE | 0.8 mM | 3 µl | 3 µl |
| RR-11a-8PEG-PA-Glu(DMA)-amide(see Example 17) | 17 mM | 0 µl | 20 µl |

A 3 ml screw cap glass vial (Teflon lined cap) is charged with the above lipids and vortexed briefly. The chloroform is evaporated under a stream of Argon until a opaque film of the lipids is obtained. Then the vial is placed in a desiccator under vacuum for 10 minutes. To the dry film is added 1000 uL of DPBS 1× and the content is vortexed until a homogenous milky suspension is obtained (3-4 min). This is followed by bath sonication in a Branson 1510 model for 5 minutes to obtain a cloudy suspension. This suspension is then probe sonicated in a Branson Model 4C15 at a 30% of full amplitude for 30 seconds (avoiding foaming) to obtain a nearly translucent suspension of liposomes. The suspension is high pressure extruded though 100 nm polycarbonate membrane (Avanti No 610005) Finally the suspension is steril filtered though 0.22 µm Millex-GV membrane filters and stored in a steril vial at 4° C. The Z avg. hydrodynamic diameter of MS-15-0 and 15-4 is 101 and 99 um (Malvern ZetaSizer instrument), respectively.

Example 20: Legumain Targeting of RR11a Decorated Liposomes

Legumain targeting experiments are performed according to the following protocol employing the liposomal formulations of Example 19:

Day 1 seed 3.12×10e4 4T1 cells/cm2 on untreated glass slide
Day 2 add 100 uM CoCl2; incubate 24 h
Day 3 add 100 ul liposomes (10e12 NPs/ml); incubate 2 h;
add 5 ug/ml Hoechst 33342; incubate 20 min; mount and analyze with a fluorescent microscope Cell culture medium: RPMI 1640 1× with L-glutamine, supplemented with 10% FBS, 10 mM Hepes, 0.075% w/v sodium bicarbonate and 1 mM sodium pyruvate.

Figure 2:
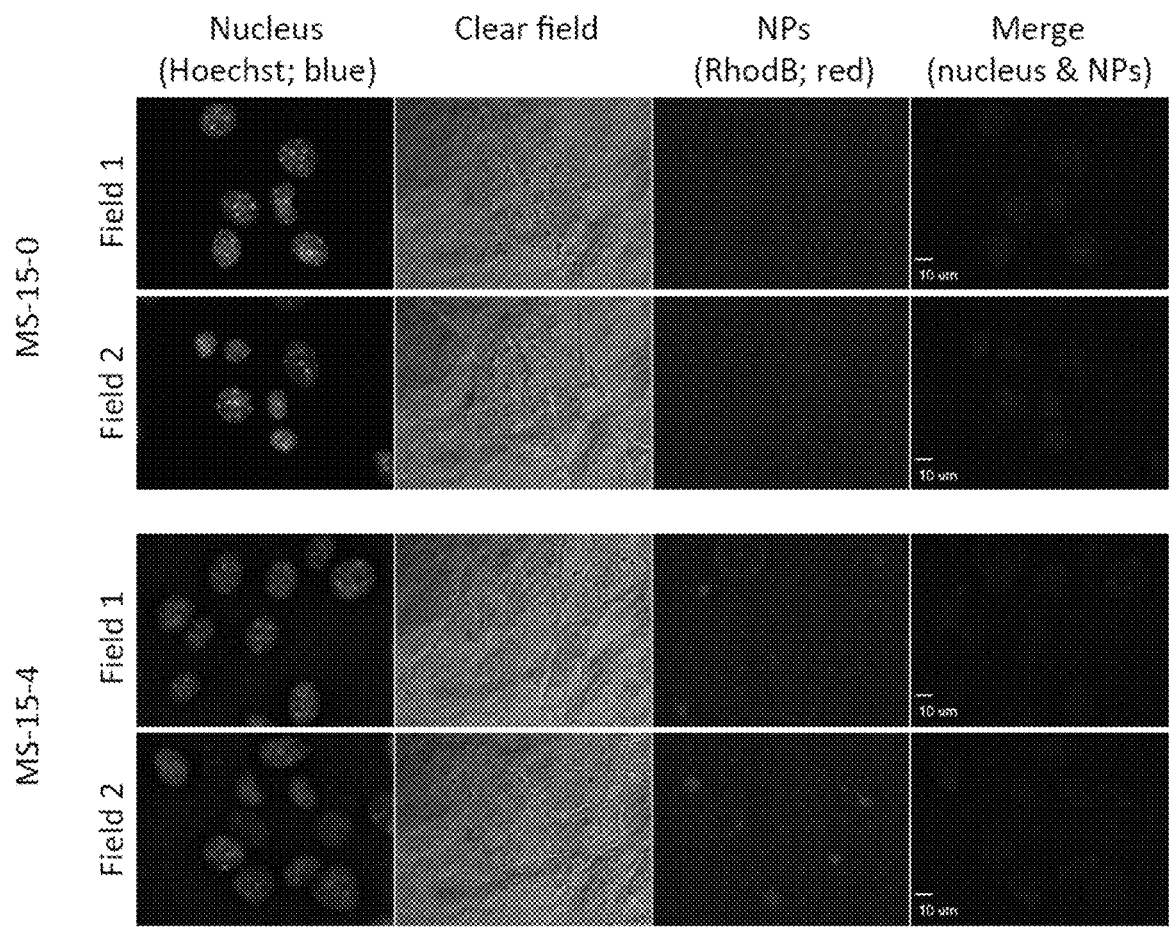
FIG. 2. Legumain targeting experiments of RR11a decorated liposomes (MS 15-4) in comparison to control liposomes (MS 15-0) according to Example 20.

Pictures are acquired from random fields from each portaobjects, using 63× objective, 2×2 bin, 500 ms for Hoechst, 1000 ms for RhodB and 100 ms clear field, and 20-30 images stack with 0.5 um height focus step around nucleus focus point for image deconvolution analysis. FIG. 2 respresents one of the 20-30 images from the stack, after deconvolution, showing an intermediate focus point. Clearly the data show colocalization of RhB-DOPE with cells and therefore demonstrate that liposomes made with RR-11a-8PEG-PA-Glu(DMA)-amide target these cells effectively compared to the non-targeted control.

Example 21: Synthesis of Antibody (Fc Unit) Targeting Lipid, Disulfide Bridged Decapentapeptide H-Glu(DMA)-Ala-Asp-Cys-Ala-Trp-his-Leu-Gly-Glu-Leu-Val-Trp-Cys-Thr-OH 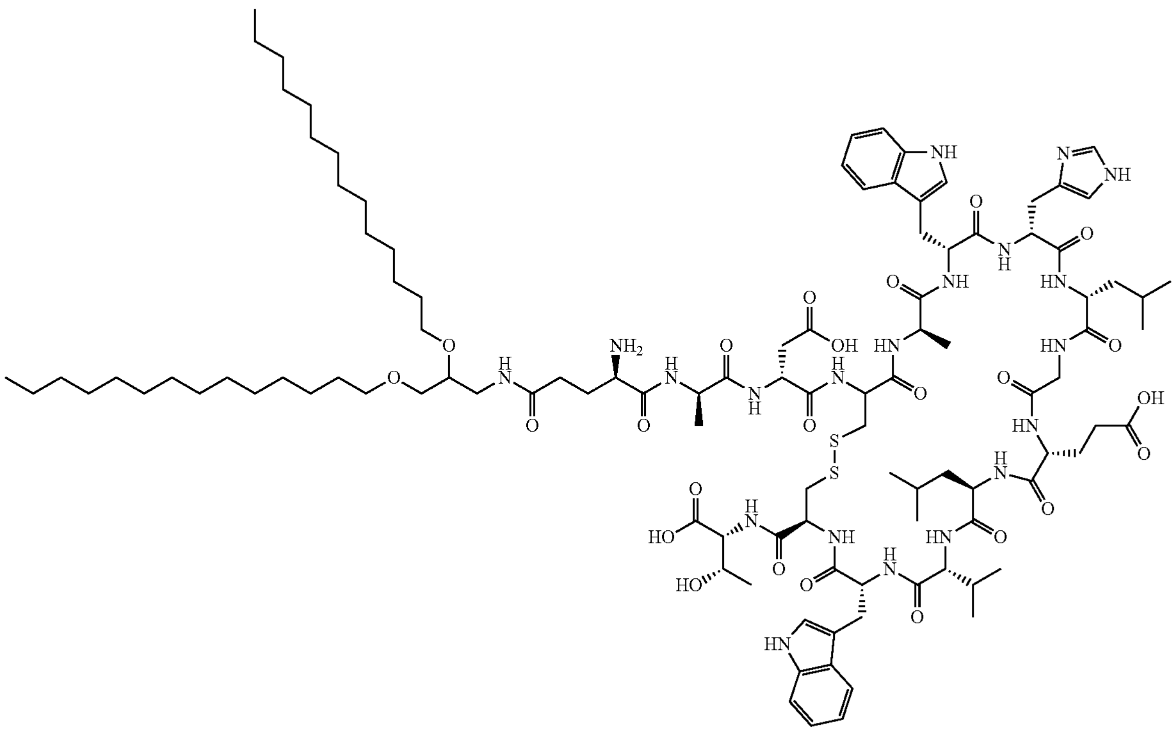 [SMILES: CCCCCCCCCCCCCCOCC(CNC(=O)CC[C@@H](N)C(=O)N[C@H](C)C(=O)N[C@H](CC(=O)O)C(=O)NC1CSSC[C@H](C(=O)N[C@@H](C(=O)O)[C@H](C)O)NC(=O)[C@@H](Cc2c[nH]c3ccccc23)NC(=O)[C@@H](C(C)C)NC(=O)[C@@H](CC(C)C)NC(=O)[C@@H](CCC(=O)O)NC(=O)CNC(=O)[C@@H](CC(C)C)NC(=O)[C@@H](Cc2c[nH]cn2)NC(=O)[C@@H](Cc2c[nH]c3ccccc23)NC(=O)[C@@H](C)NC1=O)OCCCCCCCCCCCCCC] (a) Synthesis of Linear H-Glu(DMA)-Ala-Asp-Cys-Ala-Trp-his-Leu-Gly-Glu-Leu-Val-Trp-Cys-Thr-OH The solid phase peptide synthesis is carried out with solid phase synthesizer ABI 431A following the Fmoc/tBu strategy (Atherton E., et. al., *J. Chem. Soc., Chem. Comm.,* 539 (1978)), H-Thr(tBu)-2-ClTrt (0.5 g, 0.25 mmole) is used as the base resin. The amino acid derivatives used in their chronological order are Fmoc-Cys(Trt)-OH, Fmoc-Trp(Boc)-OH, Fmoc-Val-OH, Fmoc-Leu-OH, Fmoc-Glu(OtBu)-OH, Fmoc-Gly-OH, Fmoc-Leu-OH, Fmoc-His(Trt)-OH, Fmoc-Trp(Boc)-OH, Fmoc-Ala-OH, Fmoc-Cys(Trt)-OH, Fmoc-Asp(OtBu)-OH, Fmoc-Ala-OH and Fmoc-Glu(DMA)-OH. Coupling is performed by Fmoc-Xaa-OH/Trimethylpyridine/HBTU (4 eq.:4 eq.:3.6 eq.), except Fmoc-Glu(DMA)-OH which is coupled using DIPEA/PyBOP (4.8 eq.:7.2 eq.:4.8 eq.). The removal of the Fmoc protection is achieved by 20% piperidine in DMF. Alternating washing steps three times with dimethylformamide are employed after each coupling and de-protection step respectively. The Fmoc-SPPS yields 1.4 g of linear peptide resin.

The linear decapentapeptide is cleaved from the resin by a mixture of trifluoroaceti acid/triisopropylsilane/dithioerythritol/water (92.5:2.5:2.5:2.5, 14 ml) during 2.5 hours. After filtration the filtrate is diluted with 140 ml diisopropylether. The brownish solid is filtered off and dried in vacuo: 485 mg, 37% of theory, ESI-MS: monoisotopic $M_{W\ calc.}$=2198.2, $M_W$ $[M+2H]^{2+}$=1099.6.

(b) Synthesis of Disulfide Bridged H-Glu(DMA)-Ala-Asp-Cys-Ala-Trp-his-Leu-Gly-Glu-Leu-Val-Trp-Cys-Thr-OH 10 mg of the brownish solid obtained under Example 21 a) are dissolved in 10 ml methanol and brought to pH 8 by the addition of DIPEA. The solution is stirred under oxygen atmosphere over night. Evaporation of the solution provids the final product as a brownish solid in quantitative yield. ESI-MS: monoisotopic $M_{W\ calc.}$=2196.2, $M_W$ $[M+2H]^{2+}$=1098.6.

Example 22: Preparation of RR11a Decorated Liposomes without Extrusion

RR11a decorated liposomes (MS-32-1 to MS-32-10) are composed from the following lipid solutions:

A 3 ml screw cap glass vial (Teflon lined cap) is charged with the above lipids and vortexed briefly. The chloroform is evaporated under a stream of Argon until a opaque film of the lipids is obtained. Then the vial is placed in a desiccator under vacuum for 10 minutes. To the dry film is added 1000 uL of DPBS 1× and the content is vortexed until a homogenous milky suspension is obtained (10 min). This is followed by bath sonication in a Branson 1510 model for 5 minutes to obtain a cloudy suspension. This suspension is then probe sonicated in a Branson Model 4C15 at a 40% of full amplitude for 30 seconds (avoiding foaming) to obtain a nearly translucent suspension of liposomes. Finally the suspension is steril filtered though 0.22 μm Millex-GV membrane filters and stored in a steril vial at 4° C. The Z avg. hydrodynamic diameter and PDI are determined using a Malvern ZetaSizer instrument:

| lipid | concentration in chloroform [mM] | MS-32-1 | MS-32-2 | MS-32-3 | MS-32-4 | MS-32-5 Volume [μl] | MS-32-6 | MS-32-7 | MS-32-8 | MS-32-9 | MS-32-10 |
|---|---|---|---|---|---|---|---|---|---|---|---|
| DOPE | 33 | | | | | 35 | | | | | |
| DSPC | 33 | | | | | 35 | | | | | |
| Cholesterol | 33 | | | | | 35 | | | | | |
| RhB-DOPE | 0.8 | | | | | 3 | | | | | |
| MPEG2000-DOPE | 18 | — | — | 15 | 15 | — | — | 15 | 15 | — | — |
| RR-11a-Glu(DMA)-amide (see Example 16) | 24 | — | — | — | — | 15 | — | 15 | — | — | — |
| RR-11a-8PEG-PA-Glu(DMA)-amide | 17 | 15 | — | 15 | — | — | — | — | — | — | — |
| RR-11a-36PEG-PA-Glu(DMA)-amide | 9 | — | — | — | — | — | 15 | — | 15 | 35 | 70 |
| RR-11a-8PEG-PA-Glu(DMA)-NH-MPEG2k (see Example 15) | 9 | — | 15 | — | 15 | — | — | — | — | — | — |
| Z avg. hydrodynamic diameter | | 204.9 | 115.1 | 109.0 | 98.9 | 179.8 | 144.6 | 227.0 | 100.6 | — | — |
| PDI | | 0.5 | 0.2 | 0.2 | 0.19 | 0.25 | 0.28 | 0.47 | 0.18 | — | — |

The invention claimed is:

1. A carrier system comprising a compound of formula I

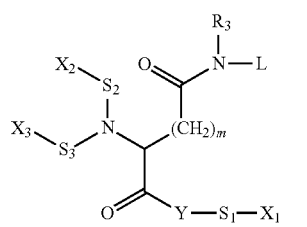

wherein
Y represents O, N, S or a covalent bond,
$S_1$, $S_2$, $S_3$ represent independently of each other a covalent bond or a spacer group,
$X_1$, $X_2$, $X_3$ represent independently of each other H or a ligand group or any two of $X_1$, $X_2$, $X_3$ may together form a ligand group, wherein at least one of $X_1$, $X_2$, $X_3$ is a legumain targeting ligand group,
L is a group of formula (a)

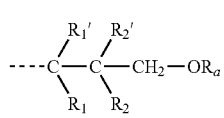

wherein the dashed line represents the linkage to N,
$R_1$ represents H or a group of formula —$(CH_2)_2$—$OR_{b1}$,
$R_1'$ represents H or a group of formula —$(CH_2)_2$—$OR_{b2}$,
$R_2$ represents H or a group of formula —$CH_2$—$OR_c$,
$R_2'$ represents H or a group of formula —$OR_d$ or —$CH_2$—$OR_d$,
$R_3$ represents H or a group of formula —$(CH_2)_2$—$OR_e$ or —$(CH_2)_3$—$OR_e$,
$R_a$, $R_{b1}$, $R_{b2}$,
$R_c$, $R_d$, $R_e$ represent independently of each other a saturated or unsaturated, straight or branched hydrocarbon chain,
m is 1, 2 or 3,
with the proviso that at least one of $R_1$, $R_1'$, $R_2$, $R_2'$, $R_3$ is not H,
and
wherein at least one of the following conditions is satisfied:
the carrier system comprises a pharmaceutically active agent in a solvated form;
or
the carrier system comprises one or more pteroyl derivatives and/or aza-peptide derivatives;
or
the carrier system has been lyophilized or freeze-dried and therefore has enhanced stability;
or
wherein at least one of $X_1$, $X_2$, $X_3$ is a ligand that is capable of binding to an antibody, antibody fragment, engineered antibody or an antibody mimic.

2. The carrier system according to claim 1, which comprises a pharmaceutically active agent in a solvated form.

3. The carrier system according to claim 1, which comprises one or more pteroyl derivatives and/or aza-peptide derivatives.

4. The carrier system according to claim 1, which has been lyophilized or freeze-dried and therefore has enhanced stability.

5. The carrier system according to claim 1, wherein at least one of $X_1$, $X_2$, $X_3$ is a ligand that is capable of binding to an antibody, antibody fragment, engineered antibody or an antibody mimic.

6. The carrier system according to claim 1, wherein $R_3$ is H, and L is a group of formulas (b) or (c)

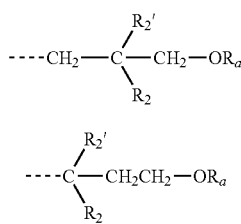

wherein the dashed line represents the linkage to N, and S₁, S₂, S₃, X₁, X₂, X₃, Y, Rₐ, and m are defined as for formula I, with the proviso that in formula (b) one of R₂ and R₂' is not H, and in formula (c) one of R₁ and R₁' is not H, and at least one of X₁, X₂, X₃ is a legumain targeting ligand group.

7. The carrier system according to claim 6, wherein L is a group of formula (b1), (b2), (b3) or (b4):

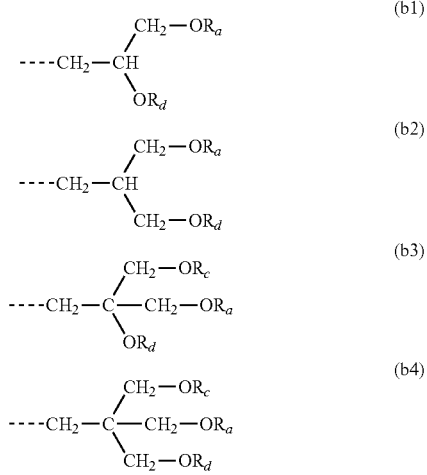

wherein the dashed line represents the linkage to N, and wherein Rₐ, Rᵤ and R_d are independently of each other a saturated or unsaturated, straight or branched hydrocarbon chain.

8. The carrier system according to claim 6, wherein L is a group of formula (c1) or (c2):

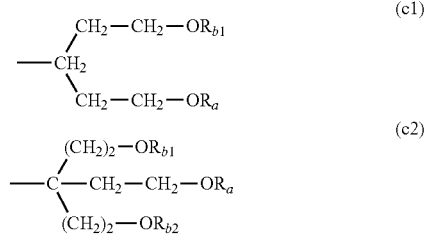

wherein the dashed line represents the linkage to N, and wherein Rₐ, R_{b1}, R_{b2} are independently of each other a saturated or unsaturated, straight or branched hydrocarbon chain.

9. The carrier system according to claim 1, wherein R₁, R₁', R₂, R₂' are H, R₃ is a group of formula —(CH₂)₂—OR_e or —(CH₂)₃—OR_e, and S₁, S₂, S₃, X₁, X₂, X₃, Y, Rₐ, and m are defined as for formula I.

10. The carrier system according to claim 1, wherein Rₐ, R_{b1}, R_{b2}, R_c, R_d, R_e are independently of each other straight or branched C(10-22)alkyl, C(10-22)alkenyl or C(10-22)alkynyl.

11. The carrier system according to claim 10, wherein C(10-22)alkenyl and C(10-22)alkynyl have 1, 2, 3 or 4 unsaturated bonds.

12. The carrier system according to claim 10, wherein C(10-22)alkenyl and C(10-22)alkynyl have 1 or 2 unsaturated bonds.

13. The carrier system according to claim 1, wherein the carrier system is a microparticulate or a nanoparticulate material.

14. The carrier system according to claim 13, wherein the microparticulate or a nanoparticulate material is a liposome or a micelle, comprising at least one compound of formula I and optionally one or more other co-lipids.

15. The carrier system according to claim 13, wherein the microparticulate or a nanoparticulate material is a lipid vesicle, a nanoparticle, a nanosphere and/or a nanorod, comprising at least one compound of formula I and optionally one or more other co-lipids.

16. The carrier system according to claim 15, wherein the lipid vesicle further contains at least one bioactive agent enclosed or embedded within its internal void or adsorbed onto or attached to its surface.

17. The carrier system according to claim 1, wherein the spacer group is polyethylene glycol or an end-capped polyethylene glycol.

18. The carrier system according to claim 1, wherein the at least one of X₁, X₂, X₃ that is a legumain targeting ligand group is RR11a.

19. The carrier system according to claim 1, wherein the carrier system is a liposome, and the at least one of X₁, X₂, X₃ that is a legumain targeting ligand group is RR11a.

20. The carrier system according to claim 1, wherein, in addition to at least one of X₁, X₂, X₃ being a legumain targeting ligand group, at least one further of X₁, X₂, X₃ or two of X₁, X₂, X₃ together is a targeting ligand or an antigenic ligand or a therapeutic or diagnostic ligand or a combination thereof.

21. A pharmaceutical composition comprising the carrier system according to claim 1 and a pharmaceutically acceptable carrier.

22. A drug delivery system, diagnostic system or as an antigen display system, said system comprising the carrier system according to claim 1 and a pharmaceutically acceptable carrier.

23. A method for the diagnosis of a disease by a disease specific diagnostic agent containing a legumain targeting ligand group, comprising administering to a host in need thereof a carrier system comprising a compound of formula I

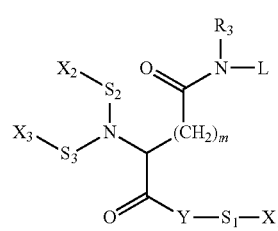

wherein

Y represents O, N, S or a covalent bond, $S_1$, $S_2$, $S_3$ represent independently of each other a covalent bond or a spacer group, $X_1$, $X_2$, $X_3$ represent independently of each other H or a ligand group or any two of $X_1$, $X_2$, $X_3$ may together form a ligand group, wherein at least one of $X_1$, $X_2$, $X_3$ is a legumain targeting ligand group, L is a group of formula (a)

$$\text{----}\overset{R_1'}{\underset{R_1}{C}}-\overset{R_2'}{\underset{R_2}{C}}-CH_2-OR_a \quad (a)$$

wherein the dashed line represents the linkage to N, $R_1$ represents H or a group of formula $-(CH_2)_2-OR_{b1}$, $R_{1'}$ represents H or a group of formula $-(CH_2)_2-OR_{b2}$, $R_2$ represents H or a group of formula $-CH_2-OR_c$, $R_{2'}$ represents H or a group of formula $-OR_d$ or $-CH_2-OR_d$, $R_3$ represents H or a group of formula $-(CH_2)_2-OR_e$ or $-(CH_2)_3-OR_e$, $R_a$, $R_{b1}$, $R_{b2}$, $R_c$, $R_d$, $R_e$ represent independently of each other a saturated or unsaturated, straight or branched hydrocarbon chain, m is 1, 2 or 3, with the proviso that at least one of $R_1$, $R_{1'}$, $R_2$, $R_{2'}$, $R_3$ is not H, wherein at least one of Xi, $X_2$, $X_3$ is said diagnostic agent containing a legumain targeting ligand group;

or a method for modulating an immune response, comprising administering to a host in need thereof the carrier system comprising the compound of formula I, wherein at least one of $X_1$, $X_2$, $X_3$ is an antigenic agent containing a legumain targeting ligand group;

or a method for treating cancer, comprising administering to a subject in need thereof an effective amount of the carrier system comprising the compound of formula I, wherein said carrier system comprises a cancer therapeutic agent;

or a method for treating an inflammatory disease, comprising administering to a subject in need thereof an effective amount of the carrier system comprising the compound of formula I, wherein said carrier system comprises an anti-inflammatory therapeutic agent;

or a method for transporting a biologically active compound across a membrane and/or a method for delivering a biologically active compound into a cell, comprising achieving said transporting or delivery by the carrier system comprising the compound of formula I, which comprises said biologically active compound;

or a method for eliciting a psychological response from a human patient, comprising administering to said human the carrier system comprising the compound of formula I, which comprises one or more bioactive agents;

or a method for preventing a psychotic episode in a human subject, comprising administering to said human the carrier system comprising the compound of formula I, which comprises one or more antipsychotic agents;

or a method for in vitro application for growth promotion and differentiation of cells or modification of expression profiles and post-translational modification patterns of biological products manufactured in a bioreactor, comprising administering into said bioreactor the carrier system comprising the compound of formula I, which bioreactor further contains said cells or biological products;

or a method for preventing a disease in a human subject, comprising administering to said human the carrier system comprising the compound of formula I, which comprises one or more vaccines.

24. The method according to claim 23, which is for the diagnosis of a disease by a disease specific diagnostic agent containing a legumain targeting ligand group, comprising administering to a host in need thereof the carrier system comprising the compound of formula I, wherein at least one of $X_1$, $X_2$, $X_3$ is said diagnostic agent containing a legumain targeting ligand group.

25. The method according to claim 23, which is for modulating an immune response, comprising administering to a host in need thereof the carrier system comprising the compound of formula I, wherein at least one of $X_1$, $X_2$, $X_3$ is an antigenic agent containing a legumain targeting ligand group.

26. The method according to claim 23, which is for treating cancer, comprising administering to a subject in need thereof an effective amount of the carrier system comprising the compound of formula I, wherein said carrier system comprises a cancer therapeutic agent.

27. The method according to claim 23, which is for treating an inflammatory disease, comprising administering to a subject in need thereof an effective amount of the carrier system comprising the compound of formula I, wherein said carrier system comprises an anti-inflammatory therapeutic agent.

28. The method according to claim 23, which is for transporting a biologically active compound across a membrane and/or a method for delivering a biologically active compound into a cell, comprising achieving said transporting or delivery by the carrier system comprising the compound of formula I, which comprises said biologically active compound.

29. The method according to claim 23, which is for eliciting a psychological response from a human patient, comprising administering to said human the carrier system comprising the compound of formula I, which comprises one or more bioactive agents.

30. The method according to claim 23, which is for preventing a psychotic episode in a human subject, comprising administering to said human the carrier system comprising the compound of formula I, which comprises one or more antipsychotic agents.

31. The method according to claim 23, which is for in vitro application for growth promotion and differentiation of cells or modification of expression profiles and post-translational modification patterns of biological products manufactured in a bioreactor, comprising administering into said bioreactor the carrier system comprising the compound of formula I, which bioreactor further contains said cells or biological products.

32. The method according to claim 23, which is for preventing a disease in a human subject, comprising administering to said human the carrier system comprising the compound of formula I, which comprises one or more vaccines.

33. The method according to claim 23, wherein, in the compound of formula I, $R_3$ is H, and L is a group of formulas (b) or (c)

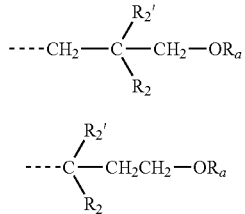

wherein the dashed line represents the linkage to N, and $S_1$, $S_2$, $S_3$, $X_1$, $X_2$, $X_3$, Y, $R_a$, and m are defined as for formula I, with the proviso that in formula (b) one of $R_2$ and $R_2'$ is not H, and in formula (c) one of $R_1$ and $R_1'$ is not H, and at least one of $X_1$, $X_2$, $X_3$ is a legumain targeting ligand group.

34. The method according to claim 23, wherein, in the compound of formula I, L is a group of formula (b1), (b2), (b3) or (b4):

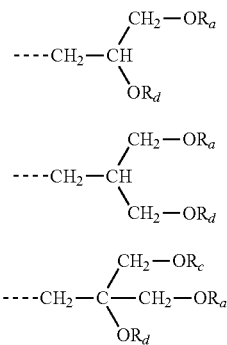

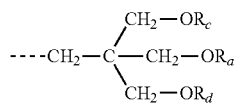

wherein the dashed line represents the linkage to N, and wherein $R_a$, $R_c$ and $R_d$ are independently of each other a saturated or unsaturated, straight or branched hydrocarbon chain;

or

L is a group of formula (c1) or (c2):

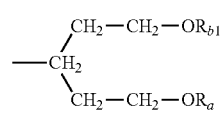

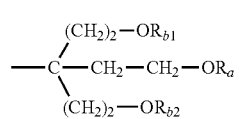

wherein the dashed line represents the linkage to N, and wherein $R_a$, $R_{b1}$, $R_{b2}$ are independently of each other a saturated or unsaturated, straight or branched hydrocarbon chain.

35. The method according to claim 23, wherein, in the compound of formula I, $R_1$, $R_1'$, $R_2$, $R_2'$ are H, $R_3$ is a group of formula —(CH$_2$)$_2$—OR$_e$ or —(CH$_2$)$_3$—OR$_e$, and $S_1$, $S_2$, $S_3$, $X_1$, $X_2$, $X_3$, Y, $R_a$, and m are defined as for formula I;

and/or $R_a$, $R_{b1}$, $R_{b2}$, $R_c$, $R_d$, $R_e$ are independently of each other straight or branched C(10-22)alkyl, C(10-22)alkenyl or C(10-22)alkynyl.

36. The method according to claim 23, wherein the carrier system has been lyophilized or freeze-dried and therefore has enhanced stability.

* * * * *